United States Patent
Kuno et al.

(10) Patent No.: US 8,557,602 B2
(45) Date of Patent: Oct. 15, 2013

(54) METHOD FOR DETECTING AND DISTINGUISHING INTRAHEPATIC CHOLANGIOCARCINOMA

(75) Inventors: Atsushi Kuno, Ibaraki (JP); Jun Hirabayashi, Ibaraki (JP); Atsushi Matsuda, Ibaraki (JP); Hisashi Narimatsu, Ibaraki (JP); Yuzuru Ikehara, Ibaraki (JP); Junichi Shoda, Ibaraki (JP); Toru Kawamoto, Ibaraki (JP)

(73) Assignees: National Institute of Advanced Industrial Science and Technology, Tokyo (JP); University of Tsukuba, Ibaraki (JP)

( * ) Notice: Subject to any disclaimer, the term of this patent is extended or adjusted under 35 U.S.C. 154(b) by 0 days.

(21) Appl. No.: 13/203,959

(22) PCT Filed: Feb. 23, 2010

(86) PCT No.: PCT/JP2010/001203
§ 371 (c)(1),
(2), (4) Date: Nov. 1, 2011

(87) PCT Pub. No.: WO2010/100862
PCT Pub. Date: Sep. 10, 2010

(65) Prior Publication Data
US 2012/0065089 A1    Mar. 15, 2012

(30) Foreign Application Priority Data
Mar. 5, 2009  (JP) ................. 2009-051935

(51) Int. Cl.
C40B 30/04  (2006.01)
G01N 33/53  (2006.01)
G01N 33/574  (2006.01)

(52) U.S. Cl.
USPC ................... 436/501; 506/9; 435/7.5

(58) Field of Classification Search
None
See application file for complete search history.

(56) References Cited

U.S. PATENT DOCUMENTS

2007/0202535 A1*  8/2007  Hirabayashi et al. .......... 435/7.1

FOREIGN PATENT DOCUMENTS

| JP | 08-184594 | 7/1996 |
|---|---|---|
| JP | 2002-323499 | 11/2002 |
| JP | 2003-116580 A | 4/2003 |
| JP | 2003-527583 | 9/2003 |
| JP | 2004-105013 | 4/2004 |
| JP | 2005-503176 | 2/2005 |
| JP | 2005-511023 | 4/2005 |
| JP | 2005-526979 | 9/2005 |
| JP | 2005-304497 | 11/2005 |
| JP | 2006-094726 | 4/2006 |
| JP | 2007-506425 | 3/2007 |
| JP | 2007-139742 | 6/2007 |
| JP | 2007-278803 | 10/2007 |
| JP | 2007-534722 | 11/2007 |
| JP | 2007-322373 | 12/2007 |
| JP | 2008-072952 | 4/2008 |
| WO | WO 2005/023301 A1 | 3/2005 |

OTHER PUBLICATIONS

Yamashita et al., (Int J. Cancer 1993; vol. 55, 82-91).*
Tateno et al., (Glycobiology, 2007; vol. 17 No. 10, pp. 1138-1146).*
Sihlbom et al., (Glycobiology,2009; vol. 19, No. 4,pp. 375-381).*
Yuan et al., (World J, Gastroenterol 2005; 11(30):4461-6.*
LMayeux et al. ("Biomarkers: Potential uses and Limitations"; NeuroRx (2004); vol. 1, pp. 182-188).*
Xia et al., (Zhonghua Zhongliu Zahi, 2008; vol. 30 issue 9, pp. 702-705 (Abstract).*
CA 15-3 Antiibody retrieved from URL http://www.abbiotec.com/antibodies/ca15-3-antibody.*
Boonla et al., "MUC1 and MUC5AC Mucin Expression In Liver Fluke-Associated Intrahepatic Cholangiocarcinoma," World Journal Of Gastroenterology, vol. 11, No. 32, pp. 4939-4946, Jan. 2005.
Dong et al., "Evaluation of Immunohistochemical Markers For Differential Diagnosis Of Hepatocellular Carcinoma From Intrahepatic Cholangiocarcinoma", Zhonghua Zhong Liu Za Zhi, vol. 30, No. 9, pp. 702-705, Sep. 2008, Abstract only.
Higashi et al., "Expression of MUC1 and MUC2 Mucin Antigens In Intrahepatic Bile Duct Tumors: Its Relationship With A New Morphological Classification Of Cholangiocarcinoma," Hepatology, vol. 30, No. 6, pp. 1347-1355, Dec. 1999.
Matsuda et al., "*Wisteria floribunda* Agglutinin-Positive Mucin 1 is a Sensitive Biliary Marker For Human Cholangiocarcinoma", Hepatology, vol. 52, No. 1, pp. 174-182, Jul. 2010.
Romani et al., "The Associated Expression Of Maspin And Bax Proteins as a Potential Prognostic Factor In Intrahepatic Cholangiocarcinoma," BMC Cancer, 6:255, pp. 1-12, Oct. 2006.

(Continued)

*Primary Examiner* — Jacob Cheu
*Assistant Examiner* — Carmencita M Belei
(74) *Attorney, Agent, or Firm* — Kenneth H. Sonnenfeld; Margaret B. Brivanlou; King & Spalding LLP (57) ABSTRACT

Disclosed are a method for early, sensitively and reliably detecting and distinguishing intrahepatic cholangiocarcinoma in a malignant tumor occurring primarily in the liver in a simple way, and a kit thereof. In the method, a glycan biomarker consisting of a lectin WFA (Wisteria floribunda Agglutinin)-binding glycoprotein derived from intrahepatic cholangiocarcinoma is used as a cancer marker to detect intrahepatic cholangiocarcinoma by detecting the cancer marker in a test specimen. The method for detecting intrahepatic cholangiocarcinoma can clearly differentiate intrahepatic cholangiocarcinoma from hepatocellular carcinoma and enables early detection and determination with a performance clinically acceptable in terms of applicability, sensitivity and precision.

7 Claims, 5 Drawing Sheets

(56) References Cited

OTHER PUBLICATIONS

Sasaki et al., "Characterization of Apomucin Expression In Intrahepatic Cholangiocarcinomas and Their Precursor Lesions: An Immunohistochemical Study," Hepatology, vol. 24, No. 5, pp. 1074-1078, Nov. 1996.

National Institute of Advanced Industrial Science and Technology et al., Supplementary European Search Report for European Patent Application No. 10748464.4, 11 pages, dated Jul. 18, 2012.

Maeda et al., "The Expression of Cytokeratins 7, 19, and 20 in Primary and Metastatic Carcinomas of the Liver," Mod. Pathology, vol. 9, No. 9, pp. 901-909, 1996.

Xu et al., "Elevation of Serum KL-6 Mucin Levels in Patients With Cholangiocarcinoma," Hepatogastroenterology, 2008, pp. 2000-2004, 55(88).

Kuno et al., "Focused Differential Glycan Analysis with the Platform Antibody-assisted Lectin Profiling forGlycan-Related Biomarker Verification," Molecular & Cellular Proteomics, Aug. 11, 2011, pp. 99-108, 8(1).

Matsuda et al., "Development of an All-In-One Technology For Glycan Profiling Targeting Formalin-Embedded Tissue Sections," Biochemical and Biophysical Research Communications, Mar. 28, 2008, pp. 259-263, 370.

Bamrungphon et al., "A New Mucin Antibody/Enzyme-Linked Lectin-Sandwich Assay Of Serum MUC5AC Mucin For The Diagnosis Of Cholangiocarcinoma," Cancer Letters, 2007, pp. 301-338, 247.

Yamashita et al., "EpCAM and α-Fetoprotein Expression Defines Novel Prognostic Subtypes of Hepatocellular Carcinoma," Cancer Research, 2008, pp. 1451-1461, 68.

Liebman et al., "Des-γ-Carboxy (Abnormal) Prothrombin As A Serum Marker Of Primary Hepatocellular Carcinoma," The New England Journal of Medicine, pp. 1427-1431, vol. 310, No. 22.

Yamashita et al., "EpCAM and a-Fetoprotein Expression Defines Novel Prognostic Subtypes of Hepatocellular Carcinoma," Cancer Research, 2008, pp. 1451-1461, 68.

Yamashita, "EpCAM-Positive Hepatocellular Carcinoma Cells Are Tumor Initiating Cells With Stem/Progenitor Cell Features," Gastroenterology, Mar. 2009, pp. 1012-1024, 136(3).

Lodi et al., "Claudin-4 Differentiates Biliary Tract Cancers From Hepatocellular Carcinomas," Modern Pathology, 2006, pp. 460-469, 19.

Liebman et al., "Des-γ-Carboxy (Abnormal) Prothrombin As A Serum Marker Of Primary Hepatocellular Carcinoma," The New England Journal of Medicine, 1984, pp. 1427-1431, vol. 310, No. 22.

Tang et al., "KL-6 Mucin Is A Useful Immunohistochemical Marker For Cholangiocarcinoma," Oncology Reports, 2007, pp. 737-741, 17.

International Search Report from PCT/JP2010/001203 dated Mar. 31, 2010.

\* cited by examiner

WFA-FITC STAINING | MY1E12-Cy5 STAINING | Merge (YELLOW INDICATES LOCATION COSTAINED BY WFA AND MY1E12)

N: NORMAL BILE DUCT
T: CHOLANGIOCARCINOMA

METHOD FOR DETECTING AND DISTINGUISHING INTRAHEPATIC CHOLANGIOCARCINOMA

TECHNICAL FIELD

The present invention relates to the provision of a method for early, sensitively and reliably detecting and distinguishing intrahepatic cholangiocarcinoma as a malignant tumor occurring primarily in the liver in a simple way and a kit therefor, and more specifically to the provision of a method for detecting and distinguishing intrahepatic cholangiocarcinoma employing a clinically applicable and simple device having performance clinically acceptable in terms of applicability, sensitivity and precision by using a glycan biomarker consisting of a lectin WFA (Wisteria floribunda Agglutinin)-binding glycoprotein as a cancer marker to detect a intrahepatic cholangiocarcinoma-specific glycan structure in the glycan biomarker as a device for early and specifically detecting intrahepatic cholangiocarcinoma, and a kit therefor.

BACKGROUND ART

Cancer is in the first place among death cause diseases in Japan, and fatalities therefrom are way ahead of those from other diseases such as cardiac diseases and brain diseases. Cancer occurs in all organs and progresses to invade and metastasize to various organs. Thus, to perform effective therapy for cancer, it is most important to treat the cancer at a treatable stage by early detection. Currently, the development of various diagnostic methods and early detection by diagnosis have become possible, which leads to early therapy to prolong life. However, despite the development of various diagnostic and therapeutic methods, invasion and metastasis from a primary lesion complicate therapy and follow a course leading to death.

Liver cancer is a malignant tumor present in the liver. Liver cancer can be divided into a primary liver cancer occurring primarily in the liver and a metastatic liver cancer resulting from the metastasis of a cancer species having occurred in an organ other than the liver into the liver. As major malignant tumors occurring in the liver (primary liver cancers), there are hepatocellular carcinoma derived from liver cells and intrahepatic cholangiocarcinoma (or cholangiocellular carcinoma) derived from biliary epithelial cells. There is also a cancer considered to be their mixed type. Hepatocellular carcinoma (HCC) is a malignant tumor derived from liver cells and accounts for 90% or more of primary liver cancers. Almost all the hepatocellular carcinoma occurs from viral hepatitis. Intrahepatic cholangiocarcinoma (ICC) is a cancer accounting for 3% of primary liver cancers and is considered to find difficulty in early detection, have a low survival rate after surgical resection, be poorly responsive to chemotherapy, and have poor prognosis.

For the early detection of liver cancer, the development of a detection device using a tumor marker has previously been under way. For hepatocellular carcinoma, to date many markers for cancer detection have been developed. For example, α1 fetoprotein (AFP) is clinically used as a tumor marker for hepatocellular carcinoma, and PIVKA-II (New Eng. J. Med. 310: 1427-1431, 1984) is also utilized as a tumor marker for hepatocellular carcinoma. Other known examples of the tumor marker for liver cancer include CEA, CA19-9, KMO-1, DuPAN-2, Span-1, CA50, SLX, basic fetoprotein (BFP), NCC-S, T-439, alkaline phosphatase isozyme, γ-GTP isozyme, IAP, TPA, β2-microglobulin, ferritin, POA, and trypsin inhibitor (Japanese Unexamined Patent Application Publication No. 2002-323499).

In recent years, many tumor markers for hepatocellular carcinoma are disclosed, which consist of genes and polypeptides expressed in hepatocellular carcinoma. For example, tumor markers for hepatocellular carcinoma are disclosed, which consist of genes and polypeptides including Gla incomplete blood coagulation factor VII (Japanese Unexamined Patent Application Publication No. 08-184594), aldolase β gene, carbamoyl phosphate synthase I gene, plasminogen gene, EST51549, albumin gene, cytochrome P-450 subfamily 2E1 gene, retinol binding protein gene or organic anion transporter C gene (Japanese Unexamined Patent Application Publication No. 2004-105013), human gene ZNFN3A1 having zinc finger and SET domains (Japanese Unexamined Patent Application Publication (Translation of PCT Application) No. 2005-511023), glypican-3 (GPC3) (Japanese Unexamined Patent Application Publication (Translation of PCT Application) No. 2005-526979) as a heparan sulfate proteoglycan, and development and differentiation enhancing factor 1 (DDEFL1) (Japanese Unexamined Patent Application Publication (Translation of PCT Application) No. 2005-503176) located in the region of chromosomal band 1p36.13 and controlling the reformation of the actin cytoskeleton.

In addition, tumor markers for hepatocellular carcinoma are disclosed, which consist of genes and polypeptides including the presence of deletion in the chromosome region 8p12, 16p13.2-p13.3, 16q23.1-q24.3 or 19p13.2-p13.3 (Japanese Unexamined Patent Application Publication No. 2006-94726), Wnt-1 encoding a secretory cysteine-rich protein family (Japanese Unexamined Patent Application Publication No. 2007-139742), genes of carbamoyl phosphate synthase L chain MGC47816 and protein HES6 comprising helix loop-helix main and orange domains (Japanese Unexamined Patent Application Publication (Translation of PCT Application) No. 2007-506425), a cell-related hepatocellular carcinoma (HCC) protein consisting of SEMA5A (semaphorin 5A), SLC2A2 (solute carrier family member), ABCC2 (ATP-binding cassette subfamily C member 2) or HAL (histidine ammonia lyase) (Japanese Unexamined Patent Application Publication (Translation of PCT Application) No. 2007-534722), or human α2,6 sialyltransferase (Japanese Unexamined Patent Application Publication No. 2007-322373).

A hepatocellular carcinoma marker in which attention is focused on a constitutive glycan group of a glycoprotein in the serum has recently been disclosed as a marker highly specific for hepatocellular carcinoma (Japanese Unexamined Patent Application Publication No. 2007-278803). The hepatocellular carcinoma marker consists of a hepatocellular carcinoma marker consisting of a trisialyl glycan disappearing or decreasing with the development of hepatocellular carcinoma; the detection of hepatocellular carcinoma using the tumor marker has been shown to be performed by using a labeled glycan and calculating the amount of the hepatocellular carcinoma marker prepared from a sample through separation using an ion-exchange column and analysis by an elution pattern in high performance liquid chromatography employing an ODS silica column.

Several tumor markers for detecting cholangiocarcinomas including intrahepatic cholangiocarcinoma are also disclosed. For example, Japanese Unexamined Patent Application Publication (Translation of PCT Application) No. 2003-527583 discloses the use of a trypsinogen activation peptide (TAP) as a marker for detecting bile duct-pancreas cancer species; Japanese Unexamined Patent Application Publication No. 2005-304497 discloses the use of at least one genomic gene selected from the group consisting of ZNF131, DOC2, DAB2, PC4, SKP2, CDH10, CDH12, TERT, CDK5, BA11, PSCA, MLZE, RECQL4, BCL1, FGF4, ITGB4, Survivin, SRC, PTPN1, PCTK1, and CTAG, as a gene marker for cholangiocarcinoma; WO2005/023301 discloses the use of an anti-glypican 3 antibody as a diagnostic agent for cholangiocarcinoma; and Japanese Unexamined Patent Application Publication No. 2008-72952 discloses the use of nucleotides constituting the base sequence of one gene except claudin 4 or at least 2 genes selected from the group consisting of (1) insulin-like growth factor-binding protein 5 (IGFBP5), (2) claudin 4 (CLDN4), (3) PDZ and LIM domain 7 (PDLIM7), and (4) Biglycan (BGN), as a marker for detecting cholangiocarcinoma. The relation between cholangiocarcinoma and claudin 4 per se is reported in "Modern Pathology 19: 460-469 (2006)".

From a standpoint of a strategy or the like for overcoming bile duct tumors including intrahepatic cholangiocarcinoma, the differential diagnosis of hepatocellular carcinoma, intrahepatic cholangiocarcinoma, and mixed-type hepatocellular carcinoma in which both of the components can be identified, in primary liver cancer is important. Cytokeratin has previously been used as a tissue marker, and attention has recently been given to new markers such as EpCAM. However, because these existing markers show positivity in not only cholangiocarcinoma but also the normal bile duct and the peripheral interstitial area, there is a need for the development of a marker more specific for cholangiocarcinoma (CytokeratinI: Oncology Rep. 17: 737-741, 2007; Cytokeratin2: Med.Pathology 9: 901-909, 1996; EpCAM1: Gastoroenterology 136: 1012-1024, 2009; EpCAM2: Cancer Res. 68: 1451-1461, 2008).

As described above, for the early detection of liver cancers such as hepatocellular carcinoma and intrahepatic cholangiocarcinoma, many markers for detecting cancer are disclosed; however, since most of the tumor markers are tumor markers for liver cancer consisting of genes or polypeptides expressed in liver cancer, they impose many constraints as detection device for early detecting and diagnosing liver cancer to be accurately and simply used on a clinical site in view of problems of clinical applicability such as a complex operation for detecting the gene expression and the detection precision for specifically detecting a cancer species and in terms of the sensitivity and precision of the differential diagnosis of a cancer species or the cancer detection, and are therefore not necessarily satisfactory. The method for detecting the occurrence of liver cancer using a gene expressed in liver cancer as a tumor marker cannot also be applied to a case where bile or the like is used as a test specimen.

PRIOR ART DOCUMENTS

Patent Documents

Patent Document 1
  Japanese Unexamined Patent Application Publication No. 08-184594
Patent Document 2
  Japanese Unexamined Patent Application Publication No. 2002-323499
Patent Document 3
  Japanese Unexamined Patent Application Publication No. 2004-105013
Patent Document 4
  Japanese Unexamined Patent Application Publication No. 2005-304497
Patent Document 5
  Japanese Unexamined Patent Application Publication No. 2006-94726
Patent Document 6
  Japanese Unexamined Patent Application Publication No. 2007-139742
Patent Document 7
  Japanese Unexamined Patent Application Publication No. 2007-278803
Patent Document 8
  Japanese Unexamined Patent Application Publication No. 2007-322373
Patent Document 9
  Japanese Unexamined Patent Application Publication No. 2008-72952
Patent Document 10
  Japanese Unexamined Patent Application Publication (Translation of PCT Application) No. 2003-527583
Patent Document 11
  Japanese Unexamined Patent Application Publication (Translation of PCT Application) No. 2005-503176
Patent Document 12
  Japanese Unexamined Patent Application Publication (Translation of PCT Application) No. 2005-511023
Patent Document 13
  Japanese Unexamined Patent Application Publication (Translation of PCT Application) No. 2005-526979
Patent Document 14
  Japanese Unexamined Patent Application Publication (Translation of PCT Application) No. 2007-506425
Patent Document 15
  Japanese Unexamined Patent Application Publication (Translation of PCT Application) No. 2007-534722
Patent Document 16
  International Publication No. WO2005/023301

Non-Patent Documents

Non-patent Document 1
  New Eng. J. Med. 310: 1427-1431 (1984)
Non-patent Document 2
  Modern Pathology 19: 460-469 (2006)
Non-patent Document 3
  Oncology Rep. 17: 737-741 (2007)
Non-patent Document 4
  Med. Pathology 9: 901-909 (1996)
Non-patent Document 5
  Gastoroenterology 136: 1012-1024 (2009)
Non-patent Document 6
  Cancer Res. 68: 1451-1461 (2008)

SUMMARY OF THE INVENTION

Object to be Solved by the Invention

To perform effective therapy for cancer, early therapy by early detection is also a most important management in liver cancer. Although as primary liver cancers there exist hepatocellular carcinoma derived from liver cells and intrahepatic cholangiocarcinoma occurring in biliary epithelial cells, early detection and suitable therapy based on accurate differential diagnosis are expected to result in cure in both of the carcinomas. Particularly, intrahepatic cholangiocarcinoma requires early detection and accurate diagnosis because it has a low survival rate after surgical resection compared to hepatocellular carcinoma. However, intrahepatic cholangiocarcinoma is difficult to early detect. In addition, it is often experienced that even when this carcinoma can be detected by diagnostic imaging such as CT scan, the differentiation thereof from hepatocellular carcinoma is difficult.

Accordingly, an object of the present invention is to provide a method for early, sensitively and reliably detecting and distinguishing intrahepatic cholangiocarcinoma as a malignant tumor occurring primarily in the liver in a simple way and a kit therefor, and more specifically to provide a method for early detecting and distinguishing intrahepatic cholangiocarcinoma with a performance clinically acceptable in terms of applicability, sensitivity and accuracy employing a cancer marker capable of clear differentiation from hepatocellular carcinoma, a method for detecting intrahepatic cholangiocarcinoma in a way applicable on a clinical site by a simple procedure, and a kit therefor.

Means to Solve the Object

In intensive studies on a cancer marker for a method of detecting intrahepatic cholangiocarcinoma applicable on a clinical site for solving the above-described problems, the present inventors have found a glycan biomarker specifically recognizing intrahepatic cholangiocarcinoma in focusing attention to the specific change of the glycan of a glycoprotein secreted from cells depending on normal cells or the type of cancer cells, based on findings of the present inventors, and searching glycan biomarkers specifically recognizing intrahepatic cholangiocarcinoma using lectin microarray analysis, that is, have found that a glycan biomarker consisting of a lectin WFA (Wisteria floribunda Agglutinin)-binding glycoprotein provides a cancer marker specifically recognizing intrahepatic cholangiocarcinoma, thereby accomplishing the present invention.

Thus, the present invention consists of a method for detecting intrahepatic cholangiocarcinoma, comprising using a glycan biomarker consisting of a lectin WFA (Wisteria floribunda Agglutinin)-binding glycoprotein derived from intrahepatic cholangiocarcinoma as a cancer marker to detect intrahepatic cholangiocarcinoma by detecting the cancer marker in a test specimen. The method for detecting intrahepatic cholangiocarcinoma according to the present invention can clearly differentiate intrahepatic cholangiocarcinoma from hepatocellular carcinoma and enables early detection and determination with a performance clinically acceptable in terms of applicability, sensitivity and precision. In addition, it enables the detection of intrahepatic cholangiocarcinoma in a way applicable on a clinical site by a simple procedure.

For the purpose of the present invention, the "lectin WFA (Wisteria floribunda Agglutinin)" in the "lectin WFA (Wisteria floribunda Agglutinin)-binding glycoprotein" as a cancer marker for specifically detecting intrahepatic cholangiocarcinoma as a glycan biomarker refers to a lectin as an agglutinin derived from Wisteria floribunda. Here, the "lectin" is defined as "a protein capable of specifically recognizing and binding to a glycan to perform bridge formation".

According to the present invention, the presence of the cancer marker in test specimens can be detected by WFA staining using a labeled lectin WFA or by a sandwich method using a sandwich of a labeled lectin WFA, a lectin WFA-binding glycoprotein as a cancer marker, and an antibody recognizing the lectin WFA-binding glycoprotein and binding thereto. Examples of the antibody recognizing the lectin WFA-binding glycoprotein and binding thereto can include antibodies obtained using CA125, N-CAM-L1, Maspin, and MUC1 as antigens.

As a result of tissue staining, MUC1, CA125, N-CAM-L1, and Maspin was observed to be specifically expressed in cholangiocarcinoma; thus, they can be not only markers in the bile and the serum but also dominant candidate marker molecules in the tissue. For the mixed-type liver cancer which occurs at a rate of several percent of the primary livers cancer and is concurrent liver cancer and intrahepatic cholangiocarcinoma, the discriminative diagnosis thereof is important because a therapeutic strategy is different between liver cancer and cholangiocarcinoma. Because cytokeratin, EpCAM, and the like currently in use are not specific for cholangiocarcinoma, it is expected that the use of the above candidate molecules as discriminative markers can contribute to an improvement in the accuracy of diagnosis. Since other candidate molecules are observed to be also expressed in cancers other than cholangiocarcinoma, they are less useful as a tissue marker; however, it is possible that a combination thereof with WFA in the bile and the serum enables the discrimination of cholangiocarcinoma patients from other disease patients and healthy individuals.

According to the present invention, fluorescently labeled WFA can be used as the "labeled lectin WFA" used when intrahepatic cholangiocarcinoma is detected by the sandwich method. When the method for detecting intrahepatic cholangiocarcinoma according to the present invention is performed using the sandwich method, the "antibody recognizing the lectin WFA-binding glycoprotein and binding thereto" is preferably provided in the form of solid-phasing the antibody on a support and sandwiching a lectin WFA-binding glycoprotein as a cancer marker with a labeled lectin WFA to carry out detection using the sandwich method. In the above sandwich method, as an alternative to solid-phasing the antibody on a support, the lectin WFA-binding glycoprotein can be presented on a reaction field where a plurality of lectins including the lectin WFA are solid-phased on a support to perform detection using a labeled product of the antibody.

The method involving solid-phasing a plurality of lectins including the lectin WFA on a support, presenting the lectin WFA-binding glycoprotein and performing detection using the labeled product of the antibody may be carried out by solid-phasing the lectin WFA directly on the support (direct method); however, as a modification of the method, lectin WFA can be changed into biotinylated WFA to prepare the resultant lectin WFA in a form solid-phased on a support coated with streptavidin (indirect method) to vastly enhance an increase in detection sensitivity and a decrease in background.

When the sandwich method is used for the measurement of the WFA-binding glycoprotein, the measurement may use ELISA, immunochromatography, radioimmunoassay (RIA), fluoroimmunoassay (FIA method), chemiluminescent immunoassay, evanescent wave analysis, or the like. These methods are well known to those of ordinary skill in the art, and any of the methods may be selected. These methods may also be performed according to conventional procedures: the setting of actual reaction conditions and the like are within the routine skill of a person skilled in the art. Of these, particularly preferred is the use of lectin/antibody sandwich ELISA in which an antibody and a lectin are used as a protein-binding substance and a glycan-binding substance, respectively.

In the sandwich method, a protein-binding substance or a glycan-binding substance is bound to a solid phase. Hereinafter, the solid-phased binding substance is referred to as a "scavenger", and the other substance is referred to as a "detector". Examples of the support (solid phase) on which a scavenger is solid-phased include a plate (e.g., a microwell plate), a microarray substrate (e.g., a slide glass for a microarray), a tube, beads (e.g., plastic beads, magnetic beads), a carrier for chromatography (e.g., Sepharose (trade name)), a membrane (e.g., a nitrocellulose membrane, PVDF membrane), and a gel (e.g., polyacrylamide gel). Among others, a plate, beads, and a membrane are preferably used; a plate is most preferably used because of its simplicity of handling. The scavenger may be solid-phased by any method provided that a sufficient binding strength is obtained; for example, it is solid-phased by covalent bonding, ionic bonding, or physical adsorption. Alternatively, a support on which a scavenger is solid-phased in advance may be used.

The detector may be indirectly or directly labeled with a labeling substance. Examples of the labeling substance include fluorescent substances (e.g., FITC, rhodamine, Cy3, and Cy5), radioactive substances (e.g., $^{13}C$, and $^{3}H$), and enzymes (e.g., alkaline phosphatase, peroxidase (horseradish peroxidase or the like), and glucose oxidase, and β-galactosidase). The detector may also be biotin-labeled while (strept)avidin being labeled with the above labeling substance to utilize the binding of biotin and (strept)avidin.

When the enzyme is used as a labeling substance, the detection is carried out by using a suitable substrate depending on the enzyme used. For example, when peroxidase is used as an enzyme, o-phenylenediamine (OPD), tetramethyl benzidine (TMB), or the like is used as a substrate; when alkaline phosphatase is used, p-nitrophenyl phosphate (PNPP), or the like is used. An enzyme reaction termination solution and a substrate-dissolving liquid which are heretofore known and properly selected depending on the enzyme selected may be used.

The scavenger forms a complex together with a WFA-binding marker glycoprotein in a body fluid sample. The signal produced by applying the detector to this complex is measured to detect and quantify the WFA-binding marker glycoprotein in a body fluid. The signal may be measured using a suitable measuring apparatus depending on the labeling substance used.

The binding of a glycan to a lectin is weak compared to that to an antibody; thus, generally, the binding constant of an antigen-antibody reaction is considered to be $10^6$ to $10^9\ M^{-1}$, while the binding constant between a glycan and a lectin is considered to be $10^4$ to $10^7\ M^{-1}$. When the lectin is used as the glycan-binding substance, the signal detection is preferably performed using an evanescent wave excited fluorescence detection method. The evanescent wave excited fluorescence detection method is a method utilizing the fact that the entrance of light into the edge (side) of a slide glass under such conditions as to produce total reflection causes the exudation of a very short-range light called evanescent wave (called near-field light) only in a near field on the order of several hundred nanometers distant from the interface, for example, between two phases with different refractive indexes such as between glass (solid phase) and water (liquid phase). This method is performed by causing an excitation light for a fluorescent substance to enter from the edge and excite only a fluorescent substance present in a near field for the observation of the fluorescence. The evanescent wave excited fluorescence detection method is described in Kuno et al., Nature Methods, 2: 851-856 (2005) and the like. For this detection, GlycoStation™ Reader 1200 (MORITEX Corporation) or the like may be used.

A lectin is used as the sugar-binding substance. The "lectin" is a generic term applied to a protein recognizing, and binding to, a specific glycan structure. Glycans are each generally formed by a plurality of types of sugars and have various and complex structures because the mode of the binding between the sugars is diverse. Many lectins derived from animals and plants are known. Examples thereof include galectins as an animal lectin family having affinity for galactose; C-type lectins as a calcium-dependent animal lectin family; annexin having certain affinity for glycosaminoglycan; leguminous lectin; and ricin. In the present invention, Wisteria-derived lectin WFA (Wisteria floribunda Agglutinin) is used.

The lectin may be properly selected depending on the glycan structure of a glycoprotein to be detected. Techniques for analyzing the glycan structure of a glycoprotein include glycan profiling by frontal affinity chromatography (FAC), a lectin microarray, or MS or $MS^n$ (mass spectrometry or tandem mass spectrometry). If the glycan structure of the glycoprotein is determined, a suitable lectin can be selected based on the information thereof. Information on lectins is available from Lectin frontier DataBase (LfDB) or the home page of Research Center for Medical Glycoscience, National Institute of Advanced Industrial Science and Technology.

An antibody is preferably used as a substance specifically binding to the protein moiety of the WFA-binding marker glycoprotein. The antibody may be a commercially available antibody; however, an antibody specific for the protein moiety of the WFA-binding marker glycoprotein may be produced by a method known per se based on the sequence information of the WFA-binding marker glycoprotein.

Based on the sequence information of the WFA-binding marker glycoprotein, the partial peptides thereof can be prepared, followed by producing an anti-WFA-binding marker glycoprotein antibody according to a method known per se as described below. These peptides may each be any peptide provided that the prepared anti-WFA-binding marker glycoprotein antibody does not cross-react with an unrelated antigen contained in a sample, and may contain the substitution, addition, deletion, or the like of one to several amino acids. For example, the peptide may be a peptide adjacent to or distant from the glycan-bound amino acid residue of the WFA-binding marker glycoprotein.

The antibody used in the present invention may be a polyclonal antibody or a monoclonal antibody. These antibodies can be produced according to a method for producing an antibody or an antiserum known per se. For the antibody production, the protein moiety of the WFA-binding marker glycoprotein is used as an antigen.

In performing the early detection of intrahepatic cholangiocarcinoma using the method for detecting intrahepatic cholangiocarcinoma according to the present invention, a clinical sample or clinical section containing bile may be used as a test specimen for detecting intrahepatic cholangiocarcinoma. It has been made possible to detect intrahepatic cholangiocarcinoma with high precision using the test specimen, permitting the early detection of the occurrence of intrahepatic cholangiocarcinoma with simplicity and high precision on a clinical site, which has been difficult when a conventional gene marker is used. The use of the method for detecting intrahepatic cholangiocarcinoma according to the present invention enables the detection of intrahepatic cholangiocarcinoma in a test specimen and the early detection and determination of intrahepatic cholangiocarcinoma occurring primarily in the liver.

The present invention encompasses a kit for detecting and/or distinguishing intrahepatic cholangiocarcinoma provided with a labeled lectin WFA and an antibody recognizing, and binding to, a lectin WFA-binding glycoprotein, used to perform the method for detecting intrahepatic cholangiocarcinoma according to the present invention. Examples of the antibody recognizing, and binding to, a lectin WFA-binding glycoprotein can include 1 or 2 or more antibodies of antibodies obtained using CA125, N-CAM-L1, Maspin, and MUC1 as antigens.

Cholangiocarcinoma markers include a tissue marker (a biopsy marker), a bile marker, and a serum marker. With regard to a phase in which the antibody recognizing and binding to a lectin WFA-binding glycoprotein can be utilized, the four molecules of MUC1, CA125, N-CAM-L1, and Maspin whose specific expression has been confirmed in cholangiocarcinoma by tissue staining are useful as tissue markers as well as serum and bile markers. Meanwhile, other antibodies not leading to cholangiocarcinoma-specific staining are probably useful as markers in the bile and serum by combination with WFA. From the results of tissue staining, the range of the antibody needs to be narrowed for adaptation to each diagnosis phase, and combination with WFA is important in the case of the bile and serum.

Preferably, the antibody recognizing, and binding to, a lectin WFA-binding glycoprotein is made into a solid-phased form and prepared in the form of a kit for detecting and/or distinguishing intrahepatic cholangiocarcinoma for lectin overlay detection. In the above sandwich method, in place of solid-phasing the antibody on a support, the lectin WFA may also be solid-phased on the support, followed by overlaying the antibody thereon for detection. When the lectin WFA is solid-phased on a support, although the lectin WFA may be directly solid-phased on the support (direct method), as a modification of the method, the lectin WFA can be changed into biotinylated WFA to prepare the lectin WFA in a form solid-phased on a support coated with streptavidin (indirect method) to vastly enhance an increase in detection sensitivity and a decrease in background.

Thus, specifically, the present invention consists of: (1) a method for detecting intrahepatic cholangiocarcinoma, comprising detecting intrahepatic cholangiocarcinoma by using a lectin WFA-binding glycoprotein as a cancer marker to detect the cancer marker in a test specimen in vitro; (2) the method for detecting intrahepatic cholangiocarcinoma according to (1), wherein the detection of intrahepatic cholangiocarcinoma using a lectin WFA-binding glycoprotein as a cancer marker involves using the lectin WFA-binding glycoprotein as a glycan biomarker to detect an intrahepatic cholangiocarcinoma-specific glycan structure in the glycan biomarker; (3) the method for detecting intrahepatic cholangiocarcinoma according to (1), wherein the detection of the presence of the cancer marker in a test specimen in vitro is carried out by WFA staining of test cells using a labeled lectin WFA; (4) the method for detecting intrahepatic cholangiocarcinoma according to (1), wherein the detection of the presence of the cancer marker in a test specimen is carried out by a sandwich method using the lectin WFA, the lectin WFA-binding glycoprotein as a cancer marker, and an antibody recognizing and binding to the lectin WFA-binding glycoprotein; and (5) the method for detecting intrahepatic cholangiocarcinoma according to (4), wherein the antibody recognizing and binding to the lectin WFA-binding glycoprotein is one or more antibodies of antibodies obtained using CA125, N-CAM-L1, Maspin, and MUC1 as antigens.

The present invention also consists of: (6) the method for detecting intrahepatic cholangiocarcinoma according to (4), wherein the sandwich method using the lectin WFA, the lectin WFA-binding glycoprotein as a cancer marker, and the antibody recognizing and binding to the lectin WFA-binding glycoprotein is carried out by using a labeled lectin WFA, or a labeled antibody recognizing and binding to an lectin WFA; (7) the method for detecting intrahepatic cholangiocarcinoma according to (4), wherein the detection of intrahepatic cholangiocarcinoma by the sandwich method by using the lectin WFA, the lectin WFA-binding glycoprotein as a cancer marker, and the antibody recognizing and binding to the lectin WFA-binding glycoprotein is carried out by lectin overlay involving solid-phasing the antibody recognizing and binding to the lectin WFA-binding glycoprotein on a support and sandwiching the lectin WFA-binding glycoprotein as a cancer marker using a labeled lectin WFA, or by antibody overlay involving solid-phasing the lectin WFA on a support and sandwiching the lectin WFA-binding glycoprotein as a cancer marker using a labeled antibody; (8) the method for detecting intrahepatic cholangiocarcinoma according to (7), wherein the detection of intrahepatic cholangiocarcinoma by antibody overlay or lectin WFA overlay is carried out by a lectin microarray detection means or an antibody microarray detection means using a microarray; (9) the method for detecting intrahepatic cholangiocarcinoma according to (1), wherein the test specimen for detecting intrahepatic cholangiocarcinoma in vitro is a clinical sample consisting of bile or blood, or a clinical section; and (10) a method for distinguishing intrahepatic cholangiocarcinoma, comprising detecting intrahepatic cholangiocarcinoma in a test specimen in vitro using the method for detecting intrahepatic cholangiocarcinoma according to (1), and distinguishing intrahepatic cholangiocarcinoma in a malignant tumor occurring primarily in the liver.

The present invention further consists of: (11) use of a lectin WFA-binding glycoprotein for use in a method for detecting intrahepatic cholangiocarcinoma comprising detecting intrahepatic cholangiocarcinoma by using a lectin WFA-binding glycoprotein as a cancer marker to detect the cancer marker in a test specimen in vitro; (12) a kit for detecting and/or distinguishing intrahepatic cholangiocarcinoma, provided with a labeled lectin WFA and an antibody recognizing and binding to a lectin WFA-binding glycoprotein, or with a labeled antibody recognizing and binding to a lectin WFA-binding glycoprotein and a lectin WFA; (13) the kit for detecting and/or distinguishing intrahepatic cholangiocarcinoma according to (12), wherein the antibody recognizing and binding to a lectin WFA-binding glycoprotein is one or more antibodies of antibodies obtained using CA125, N-CAM-L1, Maspin, and MUC1 as antigens; (14) the kit for detecting and/or distinguishing intrahepatic cholangiocarcinoma according to (12), wherein the antibody recognizing and binding to a lectin WFA-binding glycoprotein is prepared in a form solid-phased on a support, or the lectin WFA is prepared in a form solid-phased on a support; and (15) the kit for detecting and/or distinguishing intrahepatic cholangiocarcinoma according to (14), wherein the lectin WFA is changed into biotinylated WFA to prepare the lectin WFA in a form solid-phased on a support coated with streptavidin.

Effect of the Invention

The present invention provides a method for early detecting and distinguishing intrahepatic cholangiocarcinoma, difficult to differentiate from hepatocellular carcinoma and difficult to early and accurately detect, with a performance clinically acceptable in terms of applicability, sensitivity and precision and, in addition, a method for detecting intrahepatic cholangiocarcinoma in a way applicable on a clinical site by a simple procedure. Particularly, the method for detecting intrahepatic cholangiocarcinoma according to the present invention uses a clinical sample or clinical section containing bile as a test specimen for detecting intrahepatic cholangiocarcinoma and enables the detection of intrahepatic cholangiocarcinoma with high precision; thus, it permits the early detection of the occurrence of intrahepatic cholangiocarcinoma with simplicity and high precision on a clinical site, which has been difficult when a conventional gene marker is used. In addition, the kit for detecting and/or distinguishing intrahepatic cholangiocarcinoma provided for performing the method for detecting intrahepatic cholangiocarcinoma according to the present invention is a kit excellent in clinical application, which is simple and precise in the detection of intrahepatic cholangiocarcinoma and can be easily applied on a clinical site.

Among candidate marker molecules for specifically detecting intrahepatic cholangiocarcinoma, MY.1E12-binding MUC1, CA125, N-CAM-L1, and Maspin for which intrahepatic cholangiocarcinoma-specific staining is observed provide useful tissue markers for the differential diagnosis of intrahepatic cholangiocarcinoma. In conventional biopsy, the results are influenced by a method for collecting bile and a preparation production procedure as well as widely varying among diagnosing persons differentiating between shapes of cells, reducing the sensitivity thereof. Against such problems, in addition to tissue staining, cell staining is performed using a molecule including WFA to enable the utilization thereof as a marker for biopsy capable of differentiation with high precision compared to conventional biopsy.

BRIEF DESCRIPTION OF DRAWINGS

FIG. 1 is a diagram setting forth the best mode of the intrahepatic cholangiocarcinoma test using a clinical sample containing bile according to the present invention. "a" indicates a case where an antibody-immobilized well plate is used (a case where a directly or indirectly fluorescence-labeled lectin is overlaid to selectively detect a molecule binding to WFA among candidate molecules trapped by the antibody). "b" indicates a case where a WFA-immobilized well plate is used (a case where a directly or indirectly fluorescence-labeled antibody is overlaid to selectively detect a candidate molecule trapped by WFA).

FIG. 2 is a set of graphs showing the results of statistical analysis of WFA signals in comparative glycan profiling analyses. "a" indicates a case of lithiasis-associated type, and "b" indicates a case of lithiasis-unassociated type (in both cases, a signal significantly increases in the cancer site). "c" indicates the results of finding the power of test for distinguishing between cancer and non-cancer from ROC curves (the sensitivity is 84% while the specificity being 92%, showing good differentiation).

MODE FOR CARRYING OUT THE INVENTION

The present invention consists of a method for detecting intrahepatic cholangiocarcinoma, which is based on detection of WFA-binding glycoprotein derived from intrahepatic cholangiocarcinoma as a cancer marker to suggest a presence of intrahepatic cholangiocarcinoma. Sugar chain structures carried by WFA-binding glycoprotein, are specific for cholangiocarcinoma. For the purpose of the present invention, the "lectin WFA (Wisteria floribunda Agglutinin)" bound to the "lectin WFA (Wisteria floribunda Agglutinin)-binding glycoprotein" as a cancer marker for specifically detecting intrahepatic cholangiocarcinoma as a glycan biomarker refers to a lectin as an agglutinin derived from Wisteria floribunda. According to the present invention, the "lectin WFA" is used as a fluorescence labeled form or the like. Alternatively, it is used to present, capture or enrich only a WFA-binding glycoprotein group from bile by immobilization on a substrate or a support such as agarose.

According to the present invention, to identify a "lectin WFA-binding glycoprotein" (to narrow the range of a candidate molecule) in advance, it is desirable to capture and enrich a WFA-binding protein from a biological specimen such as bile using a support having WFA (Wisteria floribunda Agglutinin) immobilized on agarose or the like as a glycoprotein glycan-binding lectin. The enriched protein can be identified by proteomics using mass spectrometry or the like.

Figure 1:
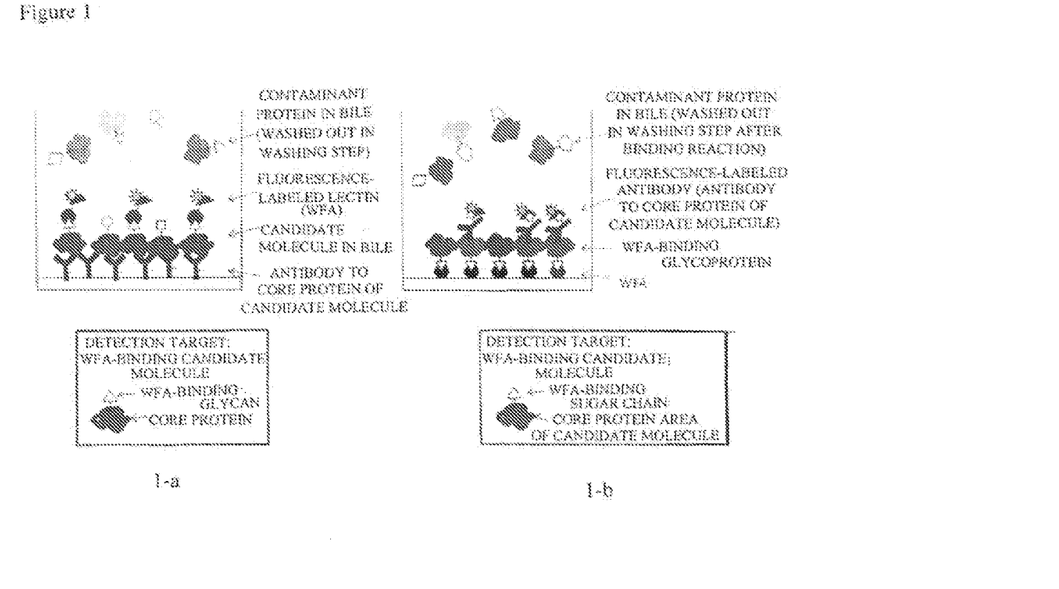

The method for detecting intrahepatic cholangiocarcinoma according to the present invention can be performed by detecting the presence of the cancer marker in a test specimen by WFA staining using a labeled lectin WFA or by a sandwich method using a sandwich of the lectin WFA, the lectin WFA-binding glycoprotein as a cancer marker and the antibody recognizing, and binding to, a lectin WFA-binding glycoprotein. The image of detecting intrahepatic cholangiocarcinoma using the sandwich method of the present invention is shown in FIG. 1. In the figure, the image of detecting intrahepatic cholangiocarcinoma when an antibody-immobilized well plate is used to overlay a directly or indirectly fluorescence-labeled lectin to selectively detect a molecule bound to WFA among candidate molecules trapped by the antibody is shown in "a" in FIG. 1, and the image of detecting intrahepatic cholangiocarcinoma when an WFA-immobilized well plate is used to overlay a directly or indirectly fluorescence-labeled antibody to selectively detect a candidate molecule trapped by WFA is shown in "b" in FIG. 1.

According to the present invention, an antibody recognizing, and binding to, a lectin WFA-binding glycoprotein is prepared in detecting intrahepatic cholangiocarcinoma using the sandwich method. The antibodies can be screened to choose the suitable among commercially available or known antibodies. Examples of the antibody recognizing, and binding to, a lectin WFA-binding glycoprotein can include antibodies obtained using CA125 (Hytest Ltd), N-CAM-L1 (R&D systems, Inc.), Maspin (Santa Cyuz Biotechnology, Inc.), and MUC1 as antigens. Among candidates marker molecules for specifically detecting intrahepatic cholangiocarcinoma, MY.1E12-binding MUC1, CA125, N-CAM-L1, and Maspin for which intrahepatic cholangiocarcinoma-specific staining is observed provide useful tissue markers for the differential diagnosis of intrahepatic cholangiocarcinoma.

In detecting intrahepatic cholangiocarcinoma using the sandwich method of the present invention, using a microarray-detecting device, a lectin overlay antibody microarray can be detected in which an antibody recognizing, and binding to, a lectin WFA-binding glycoprotein is solid-phased on an array to sandwich the lectin WFA-binding glycoprotein as a cancer marker using a labeled lectin WFA; the detection using the microarray-detecting device can be performed by an evanescent wave excited fluorescence method ("Experimental Medicine" vol. 25, no. 17 (Extra issue): 164-171, 2007). According to the method for detecting intrahepatic cholangiocarcinoma of the present invention, a sandwich method involving using a WFA-immobilized well plate to overlay a directly or indirectly fluorescence-labeled antibody to selectively detect a candidate molecule trapped by WFA can be used as a particularly preferable method for detecting intrahepatic cholangiocarcinoma.

To perform the method for detecting and/or distinguishing intrahepatic cholangiocarcinoma according to the present invention, a kit for detecting and/or distinguishing intrahepatic cholangiocarcinoma can be used, which is provided with a lectin labeled as described above and an antibody recognizing, and binding to, a lectin WFA-binding glycoprotein; however, the kit may be used by preparing, for detection, a kit in which the antibody recognizing, and binding to, a lectin WFA-binding glycoprotein is solid-phased on an array or a kit in which lectin WFA is solid-phased on an array. Examples of the antibody can include antibodies obtained using CA125, N-CAM-L1, Maspin and MUC1 as antigens.

In detecting the presence of intrahepatic cholangiocarcinoma by the method for detecting intrahepatic cholangiocarcinoma according to the present invention, a patient-derived test specimen provided for the detection of intrahepatic cholangiocarcinoma is prepared and used. According to the present invention, a clinical sample or clinical section containing bile collected from a patient is used. The method using a clinical section meets the detection of peripheral type intrahepatic cholangiocarcinoma, and the method using bile meets hepatic portal type intrahepatic cholangiocarcinoma. Using the test specimen, the presence of cancer is detected by the above detection device.

The present invention will be more specifically described below with reference to Examples. However, these Examples are not intended to limit the technical scope of the present invention.

EXAMPLE 1

[Selection of Intrahepatic Cholangiocarcinoma-Specific Glycan-Recognizing Lectin Using Lectin Array]

(Test Method)

A lectin microarray has more than 40 plant lectins exhibiting different binding specificity, which are immobilized on the same glass plate, and can be used to analyze simultaneously the interactions thereof with a sugar chain on the glycoprotein to be analyzed (Kuno et al., Nature Methods 2: 851-856, 2005). This system was used to choose suitable lectins to perform intrahepatic cholangiocarcinoma-specific staining. In this experiment, patients associated with lithiasis (cancer and non-cancer areas in the same sections), 10 patients unassociated with lithiasis (cancer and non-cancer areas in the same sections), 21 cancer areas from patients unassociated with lithiasis, and 14 non-cancer areas from patients unassociated with lithiasis were used. In brief, the total number of analyses was 45 for cancer areas and 38 for non-cancer areas. The protocol from the recovery of protein from a tissue section to the lectin array analysis thereof after fluorescent labeling was according to Matsuda et al. (Biochem. Biophys. Res. Commun. 370: 259-263, 2008).

<1. Recovery of Protein from Tissue Section>

Cancer and non-cancer areas (equivalent to 1×1 mm each) confirmed under a microscope were first scraped from each sample, and the tissue fragments were recovered in a 1.5 mL volume microtube containing 200 µl of 10 mM citric acid (pH 6.0) in advance. The resultant tissue fragment-containing solution was treated at 95° C. for 90 minutes for the dissociation of intramolecular and intermolecular crosslinking by formalin. After heat treatment, centrifugation was carried out at 20,000×g and 4° C. for 5 minutes, and the supernatant was removed. 200 µl of PBS (−) was added to the remaining tissue fragment-containing pellet (buffer exchange step). In addition, centrifugation was performed at 20,000×g and 4° C. for 5 minutes, the supernatant was then removed, and 20 µl of 0.5% NP40-PBS was added to the pellet. The pellet was grain refined by ultrasonic breaking and then reacted on ice for 60 minutes to solubilize the membrane protein. After reaction, centrifugation was performed at 20,000×g and 4° C. for 5 minutes, and the supernatant was recovered as tissue-extracted protein.

<2. Fluorescent Labeling of Protein>

All of the recovered tissue-extracted protein solution was added to Cy3-SE (from GE Healthcare) dispensed in amounts of 10 μg in PCR tubes in advance. Chemical reaction was carried out in the dark at room temperature for 1 hour, followed by adding 180 μl of a glycine-containing buffer to perform reaction in the dark at room temperature for 2 hours in order to completely terminate the reaction. The resultant solution was used as a tissue section-derived fluorescence-labeled protein solution.

<3. Lectin Array Analysis>

The tissue section-derived fluorescence-labeled protein solution was 1:2 and 1:8 diluted in a buffer for a lectin array, and 60 μl of each diluted solution was added to a reaction chamber in a lectin array. A lectin microarray plate comprising 8-reactions chamber was produced according to the method of Uchiyama et al. (Proteomics 8: 3042-3050 (2008)). After interactive reaction at 20° C. overnight, each reaction chamber was washed thrice with the buffer for a microarray and scanned according to an ordinary method. The resultant scan data were subjected to the digitalization of signals as net intensities according to an ordinary method and normalized according to the method of Kuno et al. (Journal of Proteomics and Bioinformatics 1: 68-72 (2008)) for subsequent statistical analysis.

<4. Statistical Analysis>

All of the normalized data were used in the two-group comparison test between cancer and non-cancer areas. Each data were subjected to significant tests using Welch's t-test and ROC curve analysis for each lectin and used to select a lectin showing a significant increase in signal in intrahepatic cholangiocarcinoma.

(Result)

As shown in Table 1 (the comparative glycan profiling results of glycoproteins in intrahepatic cholangiocarcinoma tissue cancer (T) and non-cancer (N) areas), statistical analysis after lectin microarray analysis showed that 5 types of lectins showed a 2-fold or more increase in binding signal in cancer areas than in non-cancer areas, and WFA had a highest specificity (4.6-fold). Accordingly, the WFA signals of the cancer and non-cancer areas of each of 14 cases of lithiasis-associated type and 10 cases of lithiasis-unassociated type were confirmed for the presence of a statistically significant difference by Welch's t-test. As a result, the significance levels of the two types were P<0.0001 and P=0.0015. From ROC curve analysis, it was found that the sensitivity was 84%, the specificity was 92%, and AUC was 0.93.

Figure 2:
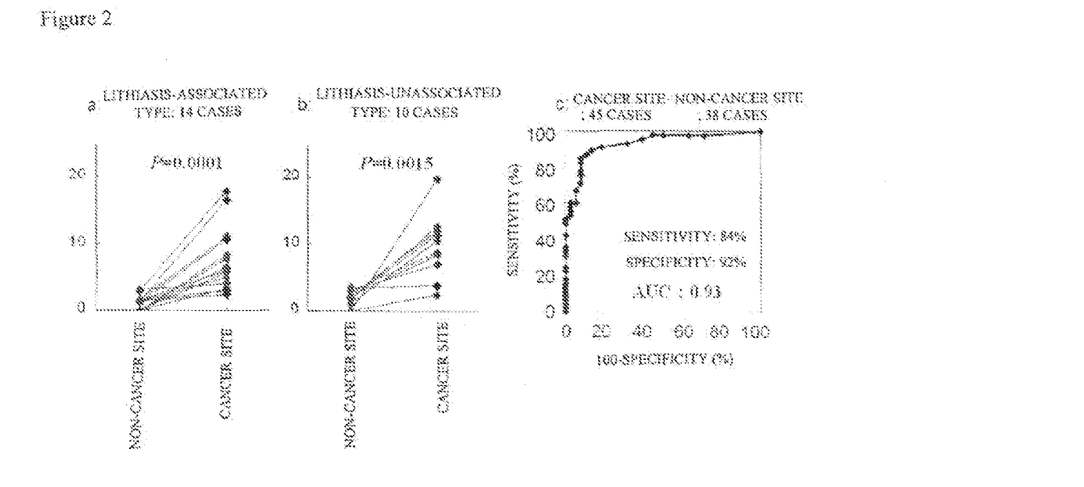

The results are shown in FIG. 2 (the results of the statistical analysis of WFA signal in the comparative glycan profiling analysis of cancer and non-cancer areas in intrahepatic lithiasis-associated type and lithiasis-unassociated type intrahepatic cholangiocarcinoma tissue sections using a lectin microarray). The above results suggested that a staining with WFA enabled to visualize the shape of intrahepatic cholangiocarcinoma in tissue section. It was also found that the WFA-binding glycan (WFA-binding glycoprotein) provided a potential specific marker for intrahepatic cholangiocarcinoma.

TABLE 1

|  | N | T | T/N | P |  |
|---|---|---|---|---|---|
|  | Mean (SEM) | Mean (SEM) | ratio | value |  |
| LTL | 8.02 (1.98) | 7.12 (1.05) | 0.888 | 0.6892 | W |
| PSA | 9.91 (1.43) | 12.70 (1.59) | 1.282 | 0.2015 | S |
| LCA | 14.53 (1.47) | 16.26 (1.54) | 1.119 | 0.4244 | S |
| UEA-I | 4.10 (0.68) | 7.19 (0.78) | 1.754 | 0.0045 | S |
| AOL | 37.63 (2.96) | 44.38 (2.47) | 1.179 | 0.0815 | S |
| AAL | 59.43 (3.87) | 67.82 (3.52) | 1.141 | 0.1120 | S |
| MAL | 3.61 (0.46) | 5.74 (0.63) | 1.590 | 0.0073 | W |
| SNA | 50.43 (2.50) | 49.50 (1.77) | 0.982 | 0.7578 | S |
| SSA | 42.11 (2.99) | 43.94 (2.41) | 1.033 | 0.6317 | S |
| TJA-I | 66.86 (3.52) | 68.00 (2.67) | 1.017 | 0.7941 | S |
| PHA-L | 2.32 (0.45) | 4.63 (0.59) | ND | ND | — |
| ECA | 5.31 (0.70) | 7.64 (0.57) | 1.439 | 0.0104 | S |
| RCA120 | 39.80 (3.37) | 41.70 (2.26) | 1.048 | 0.6412 | W |
| PHA-E | 21.39 (2.34) | 21.74 (2.39) | 1.016 | 0.9171 | S |
| DSA | 56.75 (2.93) | 61.81 (2.93) | 1.089 | 0.2287 | S |
| GSL-II | 0.58 (0.37) | 0.95 (0.44) | ND | ND | — |
| NPA | 18.62 (1.49) | 27.59 (2.22) | 1.482 | 0.0013 | W |
| ConA | 12.58 (1.53) | 14.67 (1.25) | 1.166 | 0.2886 | S |
| GNA | 23.21 (2.21) | 25.97 (2.18) | 1.162 | 0.2317 | S |
| HHL | 14.74 (1.69) | 17.00 (1.24) | 1.153 | 0.2747 | S |
| BPL | 6.51 (0.83) | 15.26 (1.27) | 2.344 | <0.0001 | W |
| TJA-II | 6.91 (0.65) | 16.41 (1.49) | 2.375 | <0.0001 | W |
| EEL | 0.73 (0.15) | 4.92 (0.94) | ND | ND | — |
| ABA | 20.77 (1.89) | 25.20 (2.39) | 1.213 | 0.1505 | W |
| LEL | 55.85 (3.26) | 49.17 (2.61) | 0.880 | 0.0667 | S |
| STL | 73.78 (3.18) | 68.42 (3.15) | 0.868 | 0.2374 | S |
| UDA | 88.82 (3.17) | 89.19 (2.57) | 1.004 | 0.9284 | S |
| PWM | 2.88 (0.48) | 5.67 (0.63) | 1.969 | 0.0004 | W |
| Jacalin | 32.54 (1.70) | 36.01 (2.41) | 1.107 | 0.2415 | W |
| PNA | 0.37 (0.13) | 1.60 (0.29) | ND | ND | — |
| WFA | 1.98 (0.30) | 9.13 (0.88) | 4.611 | <0.0001 | W |
| ACA | 12.52 (1.24) | 25.30 (1.78) | 2.021 | <0.0001 | W |
| MPA | 11.12 (0.74) | 14.05 (0.99) | 1.263 | 0.0203 | W |
| HPA | 8.04 (0.89) | 12.40 (1.64) | 1.542 | 0.0222 | W |
| VVA | 1.24 (0.37) | 3.16 (0.42) | ND | ND | — |
| DBA | 2.77 (0.78) | 5.45 (0.85) | 1.968 | 0.0108 | S |
| SBA | 0.58 (0.20) | 3.92 (0.57) | ND | ND | — |
| GSL-I | 2.87 (1.43) | 3.25 (1.16) | ND | ND | — |
| PTL-I | 0.07 (0.07) | 0.79 (0.32) | ND | ND | — |
| MAH | 3.36 (0.84) | 6.99 (0.73) | 2.080 | 0.0035 | S |
| WGA | 43.28 (3.01) | 50.16 (3.08) | 1.159 | 0.1177 | S |
| GSL-1A4 | 1.58 (0.67) | 2.80 (0.91) | ND | ND | — |
| GSL-1B4 | 5.30 (2.97) | 5.66 (2.57) | 1.068 | 0.9276 | S |

"Average" indicates the average values for 45 cancer areas and 38 non-cancer areas. The T/N ratio of 2 or more is shown in bold.

EXAMPLE 2

[Detection of Intrahepatic Cholangiocarcinoma Using Intrahepatic Bile Duct]

As shown in Example 1, it is possible to find out intrahepatic cholangiocarcinoma in a tissue section by WFA staining. In next, surgical specimen from intrahepatic cholangiocarcinoma patients but for lithiasis was used to perform as follows.

(Experimental Method)

Tissue staining with WFA was carried out as follows using a staining kit, Histo-fine (Nichirei Corporation). Formalin-fixed and paraffin embedded materials from intrahepatic cholangiocarcinoma patient were sliced (5 μm thick). Deparaffinized and rehydrated sections were washed with PBS, air-dried, immersed in a 10 mM citrate buffer (pH 6.0), and autoclaved at 121° C. for 15 minutes to dissociate intermolecular (intramolecular) crosslinking due to formalin. The treated section was allowed to stand for a while at room temperature and then repeatedly immersed for 5 minutes three times, and the tissue surface was washed. Then, the blocking reaction for endogenous peroxidase was performed by treatment with 0.3% $H_2O_2$-MeOH at room temperature for 10 minutes.

After washing with PBS (5 minutes, 3 times), the blocking reaction for suppressing the non-specific adsorption of a biotinylated lectin was performed in 1% BSA-PBS at room temperature for 10 minutes. After washing with PBS (5 minutes, 3 times), the tissue section was incubated with a biotinylated WFA solution (from Vector, suspended in HEPES to 5 μg/mL) in a moisture retention box at 20° C. for 2 hours. After washing with PBS (5 minutes, 3 times), a streptavidin solution was added thereto, which was then reacted at room temperature for 10 minutes. Further, after washing with PBS (5 minutes, 3 times), a chromogenic substrate solution was added thereto to visualize at room temperature for about 5 minutes. The resultant was immersed in Milli-Q water for 5 minutes 3 times to terminate the reaction. Finally, a nucleic acid was stained with haematoxylin at room temperature for 1 minute, and then washed with running water.

(Result)

The reaction of WFA as a convincing candidate for a intrahepatic cholangiocarcinoma diagnosis marker was studied in 25 cases of normal liver (metastatic liver cancer), 90 cases of intrahepatic cholangiocarcinoma, 10 cases of mixed-type liver cancer, and 25 cases of hepatocellular carcinoma by immunohistochemistry. As shown in Table 2 (the results of tissue staining), the expression of WFA ligand was observed in the cancerous ductal epithelium of 8 cases (32%) for normal biliary epithelium, 83 cases (88%) for intrahepatic cholangiocarcinoma, and 8 cases (80%) for the cholangiocellular carcinoma part of mixed-type liver cancer. The expression of WFA ligand was not observed in the hepatocellular carcinoma part of mixed-type liver cancer and hepatocellular carcinoma. From this, WFA was probably useful as a diagnosis marker for intrahepatic cholangiocarcinoma and mixed-type liver cancer. The presence of the WFA expression was also compared from a standpoint of clinical classification of intrahepatic cholangiocarcinoma. As a result, no change in the expression frequency of WFA ligand depending on the site (hepatic portal type or peripheral type) or the visual type (tumor-forming type, bile duct invasion type, mixed type, or intrabiliary growth type) was observed.

Figure 3:
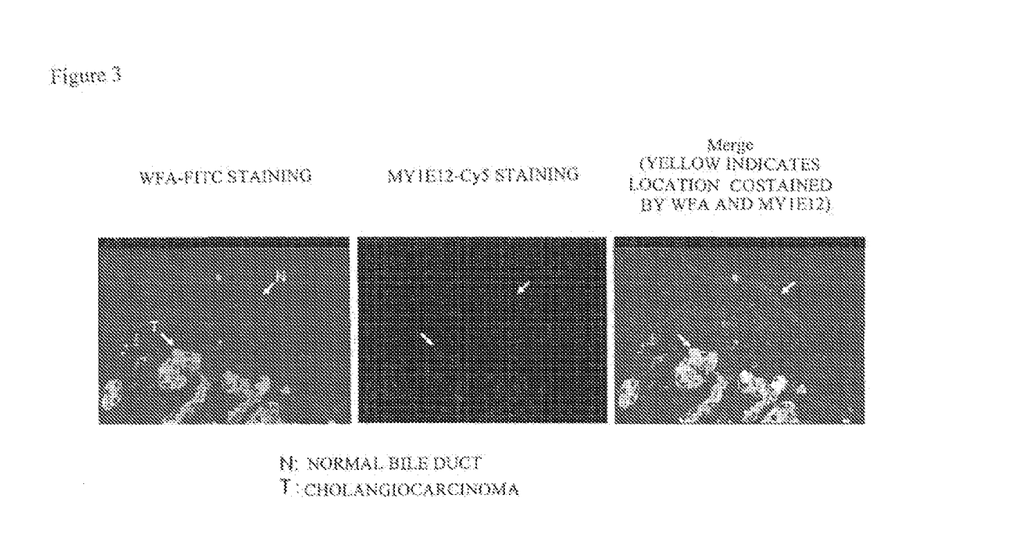
FIG. 3 is a set of photographs showing the results of the double staining of a tissue section of an intrahepatic cholangiocarcinoma patient with WFA in Example of the present invention (FITC staining, green) and MY.1E12 antibody (Cy5 staining, red) (the WFA-positive site is almost coincident with the area stained by MY.1E12).

Interestingly, the WFA-positive site is almost coincident with the area stained using MY.1E12 (J. Cancer Res., 87: 488-496, 1999; Hepatology, 30: 1347-1355, 1999) as a known intrahepatic cholangiocarcinoma marker antibody (FIG. 3: Immunohistochemistry of a tissue section from an intrahepatic cholangiocarcinoma patient: both WFA and MY.1E12 are stained in cholangiocarcinoma). Thus, MUC1 as an antigen for MY.1E12 was shown to be one of WFA-binding proteins.

EXAMPLE 3

[Detection of Intrahepatic Cholangiocarcinoma Using Cells in Bile]

Figure 4:
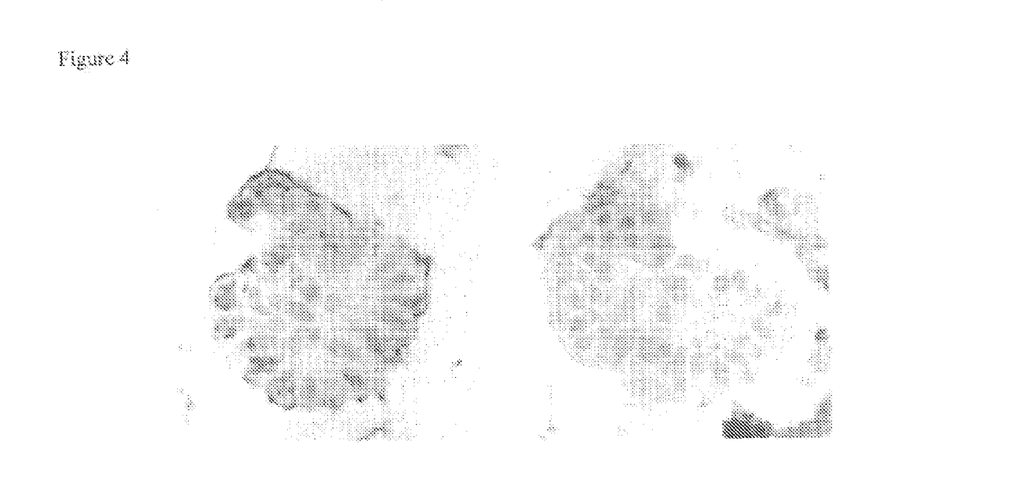
FIG. 4 is a pair of photographs showing the results of the histochemical analysis of a biopsy preparation by WFA staining in a patient in whom bile duct drainage was performed for the purpose of releasing obstructive jaundice due to intrahepatic cholangiocarcinoma with cancer cells detected by bile biopsy in Example of the present invention.

Bile duct drainage was conducted to perform releasing obstructive jaundice, and the bile collected at the time was used as a sample for analysis. When WFA staining was performed by the same procedure as in Example 2, WFA-positive cells were identified in a sample in which the presence of cancer was confirmed by histologic diagnosis and biopsy, resulting in cytologically determined cancer. However, no cells stained by WFA were identified in a sample in which histologic diagnosis and biopsy for cancer was negative (FIG. 4: the results of histochemical analysis by WFA staining in a biopsy preparation).

EXAMPLE 4

[Identification of Lectin WFA-Binding Glycoprotein]

(Experimental Method)

The capture of WFA-binding glycoprotein from a tissue section and the identification of the protein were carried out according to the following procedure. Because the difference in the protein members that identified using a mass spectrometer can occur between cases, 4 patient cases were used in this experiment, and all of the identified proteins were designated as WFA-binding proteins.

<1. Extraction of WFA-Positive Tissue Area-Derived Protein>

Six serial sections (10 μm thick) of archival formalin-fixed, paraffin-embedded liver tissue specimens from each intrahepatic cholangiocarcinoma patient were deparaffinized according to an ordinary method. The deparaffinized tissue section was washed with PBS and then air-dried. One of these sections was stained using WFA by the same method as in Example 2. The WFA-stained tissue section mounted on a slide glass was confirmed under a microscope. WFA-positive areas (about 5×5 mm square) were then scratched from 5 unstained tissue section-mounted slide glasses, and the tissue fragments were recovered in a 1.5 mL volume microtube containing 200 μL of 10 mM citric acid (pH 6.0).

The resultant tissue fragment-containing solution was treated at 95° C. for 90 minutes for the dissociation of intramolecular and intermolecular crosslinking by formalin. After heat treatment, centrifugation was carried out at 20,000×g and 4° C. for 5 minutes, and the supernatant was removed. 200 μL of PBS (−) was added to the remaining tissue fragment-containing pellet (buffer exchange step). In addition, centrifugation was performed at 20,000×g and 4° C. for 5 minutes, the supernatant was then removed, and 20 μL of

TABLE 2

| | WFA | | Localization | | |
|---|---|---|---|---|---|
| | Negative | Positive | Apical | Cytoplasmic | Stromal |
| Nomal BDE* (n = 25) | 17 (68%) | 8 (32%) | 5 (20%) | 3 (12%) | 0 (0%) |
| Cholangiocellular carcinoma (n = 90) | 7 (12%) | 83 (88%) | 45 (50%) | 54 (60%) | 8 (9%) |
| Hepatocellular - Cholangiocellular carcinoma (n = 10) | 10 (100%) | 0 (0%) | 0 (0%) | 0 (0%) | 0 (0%) |
| Hepatocellular Cholangiocellular | 2 (20%) | 8 (80%) | 2 (20%) | 6 (60%) | 0 (0%) |
| Hepatocellular carcinoma (n = 25) | 25 (100%) | 0 (0%) | 0 (0%) | 0 (0%) | 0 (0%) |

*BDE: Bile Duct Epithelia 0.5% NP40-PBS was added to the pellet. The pellet was sonicated and then reacted on ice for 60 minutes to solubilize the membrane protein. After reaction, centrifugation was performed at 20,000×g and 4° C. for 5 minutes, and the supernatant was recovered as a tissue-extracted protein solution.

<2. Capture of WFA-Binding Protein>

First, 25 μg of biotinylated WFA was immobilized on streptavidin-immobilized magnetic beads (Dynabeads MyOne Streptavidin T-1 from Dynabeads, 100 μL) to make WFA-immobilized magnetic beads. To absorb proteins non-specifically binding to the beads, the tissue-extracted protein solution was preliminary reacted with the streptavidin-immobilized magnetic beads for 1 hour and the obtained supernatant was then added to the WFA-immobilized magnetic beads, and the mixture was subjected to shaking reaction at 4° C. overnight. After binding reaction, beads were captured using a magnet and washed twice with 1 mL of 1% Triton X-100-containing PBS. 100 μL of an elution buffer (0.1% SDS-containing PBS) was added to the washed beads and then heat treated for 5 minutes to elute a WFA-binding protein. This elution fraction was used as a WFA-binding protein solution.

<3. Identification of WFA-Binding Protein>

The WFA-binding protein solution obtained in the step 2 was concentrated by TCA treatment. A total amount of the concentrated protein solution was subjected to SDS polyacrylamide gel electrophoresis using a 5-20% polyacrylamide gradient gel. After separation by electrophoresis, protein-staining bands were visualized by silver staining and cut from the gel by an ordinary method. By an ordinary method, proteins in the gel were fragmented into peptides by trypsin treatment, and after extraction from the gel and desalting, each peptide fragment was subjected to the protein identification using a mass spectrometer.

(Result)

From the above experiment using 4 cases of intrahepatic cholangiocarcinoma, 171 molecules were identified as candidate WFA-binding protein molecules. From their availability of antibodies in a commercial manner, 47 molecules of these candidate molecules were used for the subsequent selection experiment. By using a scoring method based on detailed information on each molecule, high-scored molecules were selected as one of the most dominant candidate molecules.

<Scoring Method (16 Full Marks)>

(1) 3 points are added when it is expressed in intrahepatic cholangiocarcinoma based on the expression information of the molecule in each tissue (info).

(2) 3 points are added when it has a signal sequence because a secretory protein is essentially targeted (S).

(3) 3 points are added when its expression in intrahepatic cholangiocarcinoma and its expression in a hepatocellular carcinoma tissue were confirmed in Protein Human Atlas (HUPO) in which expression information at the protein level was available, and 2 points are further added when it is also not expressed in a normal tissue (Hu).

(4) 1 point is added when its glycosylation modification is reported (Up).

(5) 2 points are added when it was reported to be a cancer-associated molecule or a change in its expression was confirmed depending on cancer development. One point is further added when the report is related to CCC and 1 point further added when its expression in bile is also reported (J).

(Result)

The results are shown in Table 3. The 6 molecules of CA125, N-CAM-L1, Maspin, Lactoferrin, Collagen IV, and Cathepsin W got total scores of 8 points or more (out of 16); thus, in addition to MUC1, these were determined to be most dominant candidate molecules for WFA-binding proteins specifically expressed in intrahepatic cholangiocarcinoma.

TABLE 3

| Protein name | Scoring Result | | | | | | | |
|---|---|---|---|---|---|---|---|---|
| | N— | O— | info | S | Hu | Up | J | score |
| CA125 | 69 | — | | | 3 + 2 | 1 | 2 + 1 + 1 | 10 |
| collagen type IV | 1 | 12 | | 3 | 3 | | 2 | 8 |
| cathepsin W | 1 | 3 | | 3 | 3 + 2 | | | 8 |
| N-CAM L1 | 6 | 15 | 3 | 3 | 3 + 2 | 1 | 2 + 1 + 1 | 15 |
| lactotransferrin | 2 | 0 | | 3 | 3 | | 2 + 1 + 1 | 9 |
| maspin | 4 | 0 | 3 | | 3 + 2 | | 2 + 1 + 1 | 11 |

EXAMPLE 5

[Selection of Candidate WFA-Binding Protein Molecule]

At this time point, although the candidates were confirmed to distinguish between cancer and non-cancer sites, their expression in the interstitial tissue and liver parenchyma was not investigated. Accordingly, the localization of a marker was determined by tissue staining to attempt further selection.

(Tissue Staining)

A formalin-fixed, paraffin-embedded tissue section (5 μm thick) from an intrahepatic cholangiocarcinoma patient was first deparaffinized. The deparaffinized tissue section was washed with PBS, and then autoclaved in a 10 mM citrate (pH 6.0) buffer at 121° C. for 15 minutes for antigen activation treatment. After washing with PBS, the resultant was immersed in 0.3% hydrogen peroxide-added methanol to inactivate endogenous peroxidases. After washing with PBS, the resultant was subjected to blocking with normal rabbit serum, followed by adding each antibody (MY. 1E12; 0.5 mg/mL, anti-CA125; 1 mg/mL, anti-Maspin; 2 mg/mL, anti-N-CAM-L1; 1 mg/mL, anti-Cathepsin W; 5 mg/mL, anti-Collagen IV; 5 mg/mL, or anti-Lactoferrin; 1 mg/mL, all of these were mouse IgG antibodies) thereto for reaction at room temperature for 1 hour. After washing with PBS, chromogenic was performed using the Histofine simple stain kit (Nichirei Corporation). After washing with sterilized water, a nucleic acid was stained with hematoxylin and the resultant was then mounted.

(Result)

Figure 5:
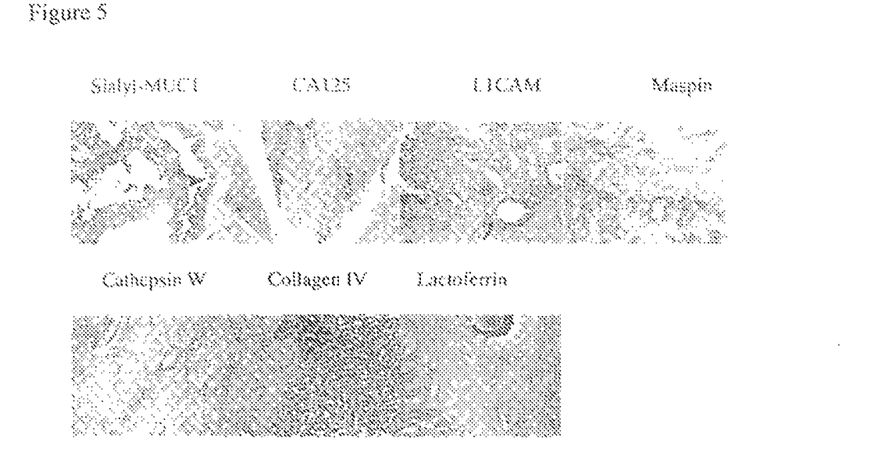
FIG. 5 is a set of photographs showing the results of tissue staining with antibodies to candidate marker molecules in a cholangiocarcinoma tissue section for the candidate molecules (MUC1, CA125, Maspin, N-CAM-L1, Lactoferrin, Cathepsin W, and Collagen IV) considered to be dominant as a result of narrowing the range of a candidate WFA-binding protein molecule by tissue staining scoring using the antibodies to the candidate molecules in test examples for narrowing the range of a candidate WFA-binding protein molecules in Example of the present invention.

Typical examples of the tissue staining of the candidate molecules are shown in FIG. 5. The expression patterns thereof are also shown in Table 4. Staining observed (+), slight but identifiable staining (−/+), and no staining observed (−) are shown. The patterns observed can be differentiated into: a most dominant candidate group (MUC1, CA125, N-CAM-L1, and Maspin) of which staining is observed specifically in cholangiocarcinoma and which seem to have the possibility of providing markers in the tissue or markers in the bile and serum; and a candidate group (Lactoferrin, Collagen IV, and Cathepthin W) which are not cholangiocarcinoma-specific markers but seem to have the possibility of providing markers in the bile or serum in combination with WFA. The former was taken to consist of final dominant candidate molecules as markers in the bile and serum as well as the tissue, and the latter, final dominant candidate molecules as markers in the bile and serum.

TABLE 4

|  | Cholangiocarcinoma | Normal Biliary Epithelium | Interstitial Tissue | Liver Cell |
|---|---|---|---|---|
| MUCI | + | − | − | − |
| CA125 | + | − | − | − |
| N-CAM-L1 | + | −/+ | − | − |
| Maspin | + | − | − | − |
| Lactoferrin | + | − | + | + |
| Collagen IV | + | + | + | + |
| Cathepsin W | −/+ | − | −/+ | −/+ |

EXAMPLE 6

[Detection of Intrahepatic Cholangiocarcinoma Using Bile 1]

As the best mode for using a glycan biomarker consisting of a WFA-binding glycoprotein derived from intrahepatic cholangiocarcinoma as a cancer marker to detect the intrahepatic cholangiocarcinoma-specific glycan structure in the glycan biomarker, a method is contemplated for detecting a glycan biomarker in a tissue lysate or bile and distinguishing intrahepatic cholangiocarcinoma by a clinically applicable and simple device having clinically acceptable performance. The results of the sandwich detection analysis of the MY.1E12 antibody-binding MUC1 molecule, which was identified as a candidate molecule in Example 2 among the 7 selected intrahepatic cholangiocarcinoma-specific candidate marker molecules, using an MY.1E12 antibody and WFA-coated well plate (see FIG. 1b) for the bile of a intrahepatic cholangiocarcinoma patient are shown below as one of the examples.

(Experimental Method)

<1. Preparation of WFA-Coated Well Plate>

100 µL of WFA dissolved in a PBS buffer (from Vector, 2.5 µg/mL) was added to each well of a microtiter plate (a 96-well flat bottom high-binding plate from Greiner) and kept at room temperature for 2 hours to immobilize WFA on the plate. Unbound WFA was washed twice with 0.1% Tween 20-containing PBS (200 µL) as a wash solution, and 200 µL of a 1% BSA-containing wash solution as a blocking agent was added. After reaction at room temperature for 2 hours, the plate was washed twice with 0.1% Tween 20-containing PBS (200 µL) to complete a WFA-coated well plate.

<2. Binding and Detection Reaction>

Protein amount in bile was first measured using a micro BCA protein quantification kit (from PIERCE). Each sample was diluted to 200 µg/mL in the above wash solution and 100 µL thereof was added to the WFA-coated well plate prepared in 1, which was then subjected to binding reaction at room temperature for 2 hours. After reaction, each well was washed 5 times with 200 µL of the above wash solution to remove unbound protein. Thereto was added 100 µL/well of a detection reagent (an MY.1E12 antibody solution) adjusted to 0.5 µg/mL in advance, which was then subjected to an antigen-antibody reaction at room temperature for 2 hours.

To remove the unbound antibody, the resultant was washed with 200 µL of the wash solution, and 100 µL/well of an anti-mouse IgG antibody-HRP solution (from Jackson immuno Research) 1:4,000 diluted in the wash solution was then added thereto, which was then incubated at room temperature for 1 hour. After washing each well 5 times with 200 µL of the wash solution, 100 µL of ULTRA-TMB solution (from Thermo) as a chromogenic substrate solution was added to each well, which was then subjected to a chromogenic reaction for 10 minutes. The reaction was terminated by adding 100 µL/well of a 1 M $H_2SO_4$ solution, followed by absorbance determination at 450 nm using a plate reader. The resultant signals (S) were digitalized in the form of S/N ratios using healthy individual serum containing no MY.1E12-binding MUC1 as a negative control (N) and used in subsequent analysis.

(Result)

Figure 6:
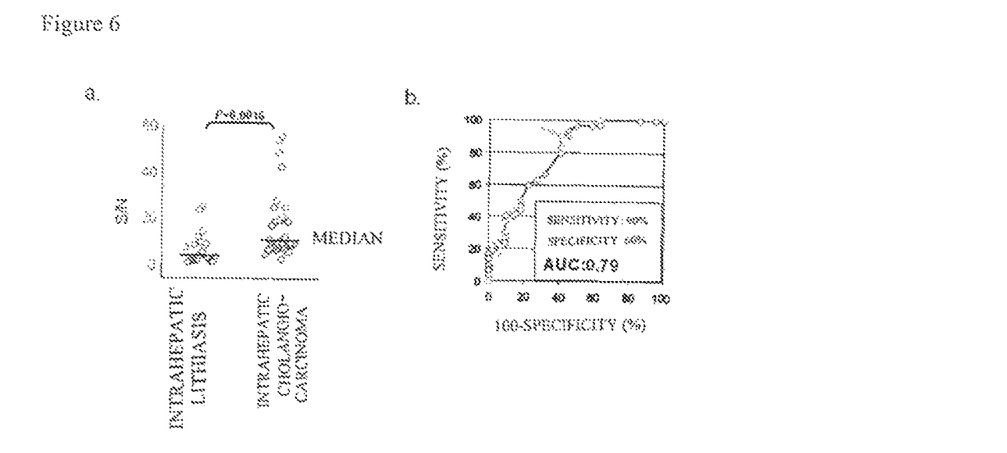
FIG. 6 is a pair of graphs showing the analysis results of selectively detecting a candidate molecule trapped by WFA by using a WFA-immobilized well plate to overlay an indirectly fluorescence-labeled MY.1E12 antibody, on biles of 30 patients with intrahepatic cholangiocarcinoma and 22 patients with intrahepatic lithiasis in test examples in Example of the present invention. "a" is a graph showing the results of digitalizing the resultant signals in the form of S/N ratios using healthy individual serum containing no MY.1E12-binding MUC1 as a negative control (N). "b" is a graph in which the power of test for distinguishing between cancer and lithiasis was found from ROC curves (the sensitivity was 90% and the specificity was 60%).

In addition to 30 cases of bile derived from intrahepatic cholangiocarcinoma patients, 22 cases of bile derived from intrahepatic lithiasis patients were analyzed. The results are shown in FIG. 6a. The S/N value is found to clearly increase in intrahepatic cholangiocarcinoma patients compared to that in intrahepatic lithiasis patients. The significance level was P=0.0016 in t-test. Accordingly, ROC curves were prepared with the intrahepatic cholangiocarcinoma patients as positivity and with the intrahepatic lithiasis patients as negativity. The results are shown in FIG. 6b. The sensitivity for distinguishing between cancer and lithiasis was 90% and the specificity therefor was 60%. This result is superior to the results obtained using any marker previously reported as shown in Table5 (comparison between the WFA-MY.1E12 sandwich ELISA method and the reported methods: italic indicates Example of the present invention; literature data are shown for a test using each existing marker). Particularly, the resultant sensitivity, i.e., the ability to detect cancer, is 90%, that is conspicuously superior to the highest value (71%) for the existing method. It is necessary that intrahepatic cholangiocarcinoma can be early detected with low false negativity, by its characteristics. That is, a high-sensitivity marker is important. In that sense, the method now developed is shown to be based on a most excellent intrahepatic cholangiocarcinoma marker.

TABLE 5

Comparison between WFA-MY.1E12 Sanwich ELISA Method and Reported Method

|  | Sensitivity (%) | Specificity (%) |
|---|---|---|
| CA19-9*[1] | 64.5 (±3.2) | 63.9 (±3.5) |
| CEA*[1,2] | 45.2 | 45.8 |
| CA125*[1] | 38.0 (±6.3) | 90.2 (±12.8) |
| Fibronectin*[3] | 57.0 | 79.0 |
| K-RAS*[4] | 31.4 | 98.0 |
| MUC5AC*[5] | 68.8 | 90.0 |
| Mac2-BP*[6] | 69.0 | 67.0 |
| *WFA-sTMUC1* | *90.0* | *59.9* |

(Italic: Example of Present Invention.)
*[1]J. Gastroenterol Hepatol. (1991), Hepatogastroenterology. (2002), Cancer. (2004)
*[2]Am. J. Surg. (1995)
*[3]Hepatogastroenterology. (2003)
*[4]Clin. Chemistry. (2004), Gtn. (2008)
*[5]Cancer Letter (2007)
*[6]Cancer (2004)

EXAMPLE 7

[Detection of Intrahepatic Cholangiocarcinoma Using Bile 2]

Figure 7:
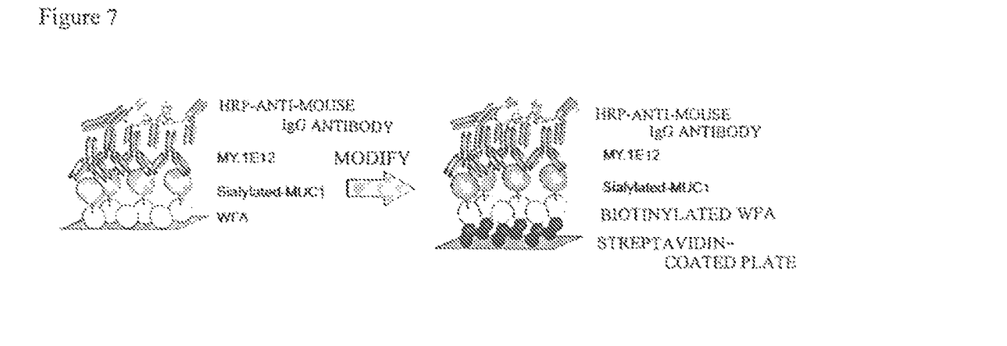
FIG. 7 is a schematic diagram showing the immobilization of a modified WFA on an ELISA plate in sandwich ELISA in which the immobilization was improved by using the streptavidin-biotin system by changing the plate into a streptavidin-coated plate (a 96-well flat bottom streptavidin-coated plate from NUNC) and the WFA to be immobilized from unlabeled WFA into a biotinylated WFA (from Vector), where formerly an unlabeled WFA was immobilized on a microtiter plate (a 96-well flat bottom high-binding plate from Greiner), in test examples of the detection of intrahepatic cholangiocarcinoma using bile in Example of the present invention.

Aiming for an enhancement in detection sensitivity and a decrease in background noise, the method for immobilizing lectin was changed from the direct method to an indirect method as shown in FIG. 7 (improved sandwich ELISA). Among the candidate molecules, the MY.1E12 antibody-binding MUC1 molecule and CA125 were investigated.

(Experimental Method)

<1. Preparation of WFA-Coated Well Plate>

50 μL of biotinylated WFA (from Vector, 20 μg/mL) was added to each well of a streptavidin-coated microtiter plate (a 96-well flat bottom plate from NUNC) and kept at room temperature for 1 hour to immobilize WFA on the plate. Unbound biotinylated WFA was washed twice with 0.1% Tween 20-containing PBS (300 μL) as a wash solution to complete a WFA-coated well plate.

<2. Binding and Detection Reaction>

Protein amount in bile was first measured using a micro BCA protein quantification kit (from PIERCE). Each sample was diluted to 400 μg/mL in the above wash solution and 50 μL thereof was added to the WFA-coated well plate prepared in 1, which was then subjected to binding reaction at room temperature for 2 hours. After reaction, each well was washed 5 times with 300 μL of the above wash solution to remove unbound protein. Thereto was added 50 μL/well of a detection reagent (an MY.1E12 antibody solution) adjusted to 0.5 μg/mL using the wash solution or a detection reagent (an anti-CA125 antibody solution) adjusted to 1.0 μg/mL using the wash solution in advance, which was then subjected to an antigen-antibody reaction at room temperature for 2 hours.

To remove the unbound antibody, the resultant was washed with 300 μL of the wash solution, and 50 μL/well of an anti-mouse IgG antibody-HRP solution (from Jackson immuno Research) 1:4,000 diluted in the wash solution was then added thereto, which was then incubated at room temperature for 1 hour. After washing each well 5 times with 300 μL of the wash solution, 100 μL of ULTRA-TMB solution (from Thermo) as reagent chromogenic substrate solution was added to each well, which was then subjected to a chromogenic reaction for 10 minutes. The reaction was terminated by adding 100 μL/well of a 1 M $H_2SO_4$ solution, followed by absorbance determination at 450 nm using a plate reader. The resultant signals (S) were digitalized in the form of S/N ratios using healthy individual serum containing no MY.1E12-binding MUC1 as a negative control (N) and used in subsequent analysis.

(Result)

Figure 8:
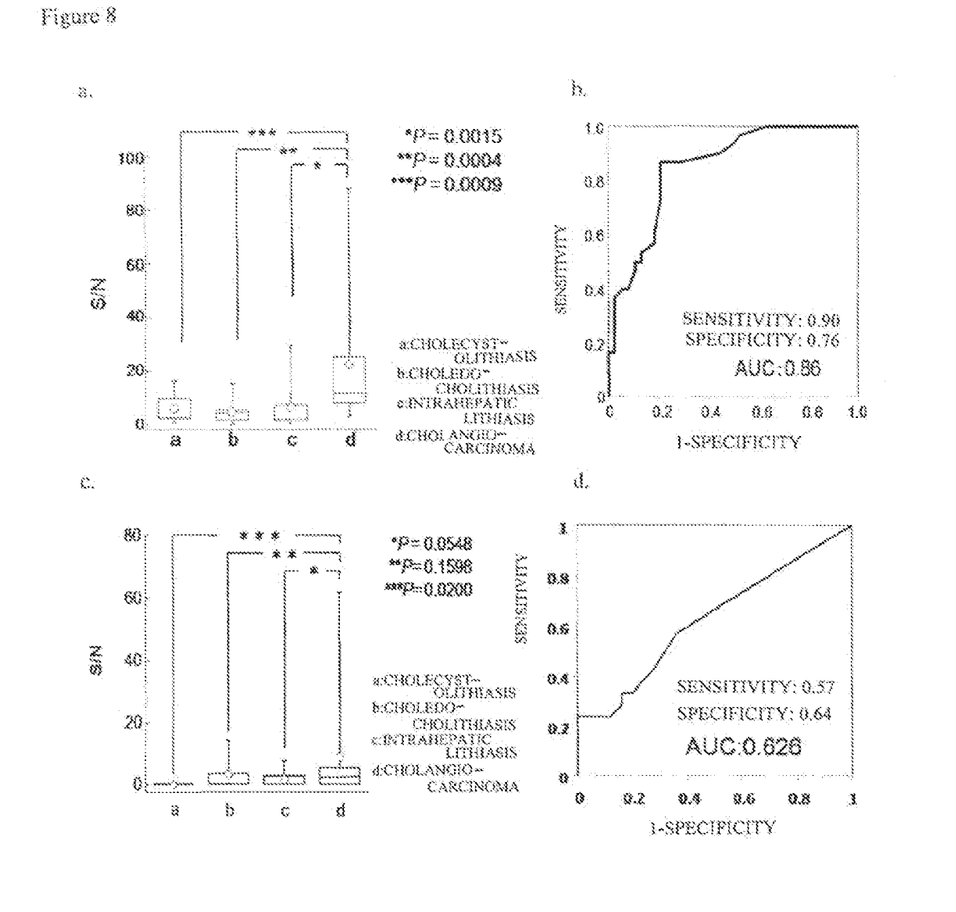
FIG. 8 is a set of graphs showing the results of WFA-MY.1E12 sandwich ELISA in immobilizing WFA by a sandwich ELISA streptavidin-biotin system using MY.1E12-binding MUC1-WFA and CA125-WFA, in test examples of the detection of intrahepatic cholangiocarcinoma using bile in Example of the present invention. "a" is a graph showing the comparative analysis of cholecystolithiasis, choledocholithiasis and intrahepatic lithiasis patients as benign disease patients and intrahepatic cholangiocarcinoma patients. "b" is a graph showing the results of finding the power of test for distinguishing between cancer and lithiasis from ROC curves based on the results of "a" (the sensitivity was 90% and the specificity was 76%). The results of WFA-CA125 sandwich ELISA in immobilizing WFA using the streptavidin-biotin system are also shown. "c" is a graph showing the comparative analysis of cholecystolithiasis, choledocholithiasis and intrahepatic lithiasis patients as benign disease patients and intrahepatic cholangiocarcinoma patients. "d" is a graph showing the results of finding the power of test for distinguishing between cancer and lithiasis from ROC curves based on the results of "c" (the sensitivity was 57% and the specificity was 64%).

In addition to 30 cases of bile derived from intrahepatic cholangiocarcinoma patients, 22 cases of bile derived from intrahepatic lithiasis patients were analyzed. The results are shown in FIG. 8a. The S/N value is found to clearly increase in intrahepatic cholangiocarcinoma patients compared to that in intrahepatic lithiasis patients. The significance level was P=0.0015 in t-test. Accordingly, ROC curves were prepared with the intrahepatic cholangiocarcinoma patients as positivity and with the intrahepatic lithiasis patients as negativity. The results are shown in FIG. 8b. The sensitivity for distinguishing between cancer and lithiasis was 90% and the specificity therefor was 76%, showing a drastically increased specificity compared to that for the direct immobilization of lectin. As shown in FIG. 8 c and d, for the WFA-CA125 sandwich ELISA, the significant difference between the lithiasis and cholangiocarcinoma patients was 57% in sensitivity and 64% in specificity.

(Discussion: Comparison with Cytology)

Table 6 (comparison between the WFA-MY.1E12 sandwich ELISA method and the bile biopsy: italic indicates Example of the present invention) shows that the results of the method for detecting and distinguishing intrahepatic cholangiocarcinoma according to the present invention is superior to the results of the diagnosis by bile biopsy conventionally performed using bile. The resultant sensitivity, i.e., the ability to detect cancer, is 83% (15/18) superior to 22% (4/18) for the bile biopsy. It is necessary that intrahepatic cholangiocarcinoma can be early detected with low false negativity, by its characteristics. That is, a high-sensitivity marker is important. In that sense, the method now developed is shown to be based on a most excellent intrahepatic cholangiocarcinoma marker.

In contrast, it was shown that WFA-CA125 sandwich ELISA was inferior in sensitivity to WFA-MY.1E12 sandwich ELISA but showed an increased positive rate depending on the biopsy class. Thus, WFA-CA125 sandwich ELISA was suggested to have the possibility of being suitable for differentiating cancer at a later progression stage than WFA-MY.1E12 sandwich ELISA.

TABLE 6

| Biopsy Class | n | Biopsy Diagnosis Result | WFA-MY.1E12 Positive Rate | WFA-CA125 Positive Rate |
|---|---|---|---|---|
| IIIa | 8 | Negative | 6/8 (75%) | 1/8 (13%) |
| IIIb-IV | 6 | Suspect | 5/6 (83%) | 4/6 (67%) |
| V | 4 | Positive | 4/4 (100%) | 4/4 (100%) |

EXAMPLE 8

[Detection of Intrahepatic Cholangiocarcinoma Using Blood]

Because the high-sensitive detection system could be established as described above, detection was subsequently attempted using blood.

(Experimental Method)

<1. Preparation of WFA-Coated Well Plate>

50 μL of biotinylated WFA (from Vector, 20 μg/mL) was added to each well of a streptavidin-coated microtiter plate (a 96-well flat bottom plate from NUNC) and kept at room temperature for 1 hour to immobilize WFA on the plate. Unbound biotinylated WFA was washed twice with 0.1% Tween 20-containing PBS (300 μL) as a wash solution to complete a WFA-coated well plate.

<2. Binding and Detection Reaction>

Each serum sample was diluted to 4 μL/100 μL in the above wash solution and 50 μL thereof was added to the WFA-coated well plate prepared in 1, which was then subjected to binding reaction at room temperature for 2 hours. After reaction, each well was washed 5 times with 300 μL of the above wash solution to remove unbound protein. Thereto was added 50 μL/well of a detection reagent (an MY.1E12 antibody solution) adjusted to 0.5 μg/mL using the wash solution in advance, which was then subjected to an antigen-antibody reaction at room temperature for 2 hours.

To remove the unbound antibody, the resultant was washed with 300 μL of the wash solution, and 50 μL/well of an anti-mouse IgG antibody-HRP solution (from Jackson immuno Research) 1:4,000 diluted in the wash solution was then added thereto, which was then incubated at room temperature for 1 hour. After washing each well 5 times with 300 μL of the wash solution, 100 μL of ULTRA-TMB solution (from Thermo) as reagent chromogenic substrate solution was added to each well, which was then subjected to a chromogenic reaction for 10 minutes. The reaction was terminated by adding 100 μL/well of a 1 M $H_2SO_4$ solution, followed by absorbance determination at 450 nm using a plate reader.

Figure 9:
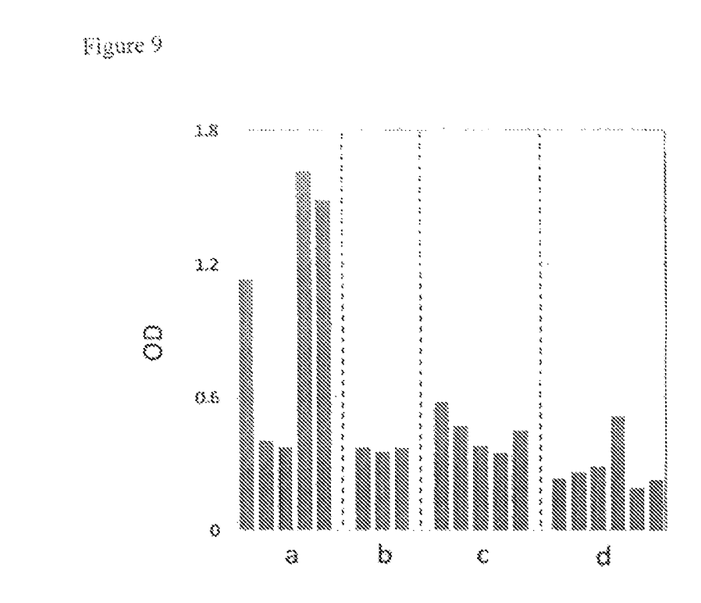
FIG. 9 is a graph showing the results of WFA-MY.1E12 sandwich ELISA in sera of patients, in test examples of the detection of intrahepatic cholangiocarcinoma using blood in Example of the present invention. "a" indicates the results obtained using sera from cholangiocarcinoma 5 patients; "b", sera from PBC patients; "c", sera from intrahepatic lithiasis patients; and "d", sera from healthy individuals.

In addition to 5 cases of sera derived from cholangiocarcinoma patients, 3 cases of sera derived from primary biliary cirrhosis (PBC) patients, 5 cases of sera derived from intrahepatic lithiasis patients, and 6 cases of sera from healthy individuals were analyzed. The results are shown in FIG. 9. It is shown that the value clearly increases in cholangiocarcinoma patients (a) compared to those in PBC patients (b), intrahepatic lithiasis patients (c), and healthy individuals (d).

The invention claimed is:

1. A method for detecting intrahepatic cholangiocarcinoma in a subject undergoing testing or screening for liver carcinoma, the method comprising:
   a) contacting a clinical specimen obtained from the subject with Wisteria floribunda Agglutinin (WFA) lectin, under conditions in which the WFA lectin specifically binds a WFA-binding glycoprotein expressed by intrahepatic cholangiocarcinoma cells to form a WFA lectin-glycoprotein complex, wherein the WFA-binding glycoprotein is a cancer marker specific for intrahepatic cholangiocarcinoma and wherein one or more antibodies obtained using MUCI, CA125, or maspin as antigens recognize and bind to the WFA-binding glycoprotein; and
   b) detecting the presence of the WFA lectin-binding glycoprotein complex, thereby detecting intrahepatic cholangiocarcinoma in the subject.

2. The method for detecting intrahepatic cholangiocarcinoma according to claim 1, wherein the detection of intrahepatic cholangiocarcinoma using the lectin WFA-binding glycoprotein as a cancer marker involves using the lectin WFA-binding glycoprotein as a glycan biomarker to detect an intrahepatic cholangiocarcinoma-specific glycan structure in the glycan biomarker.

3. The method for detecting intrahepatic cholangiocarcinoma according to claim 1, wherein the detection of the presence of the cancer marker of the lectin WFA-binding glycoprotein in a test specimen is carried out by a sandwich method which detects binding of the lectin WFA, the lectin WFA-binding glycoprotein as a cancer marker, and an antibody recognizing and binding to the lectin WFA-binding glycoprotein, wherein the antibody recognizing and binding to the lectin WFA-binding glycoprotein is one or more antibodies obtained using MUCI, CA125, or Maspin as antigens.

4. The method for detecting intrahepatic cholangiocarcinoma according to claim 3, wherein the sandwich method which detects binding of the lectin WFA, the lectin WFA-binding glycoprotein as a cancer marker, and the antibody recognizing and binding to the lectin WFA-binding glycoprotein is carried out by using a labeled lectin WFA, or a labeled antibody recognizing and binding to the lectin WFA binding glycoprotein, wherein the antibody recognizing and binding to the lectin WFA-binding glycoprotein is one or more antibodies obtained using MUCI, CA125, or Maspin as antigens.

5. The method for detecting intrahepatic cholangiocarcinoma according to claim 3, wherein the detection of intrahepatic cholangiocarcinoma by the sandwich method which detects binding of the lectin WFA, the lectin WFA-binding glycoprotein as a cancer marker, and the antibody recognizing and binding to the lectin WFA-binding glycoprotein, wherein the antibody recognizing and binding to the lectin WFA-binding glycoprotein is one or more antibodies obtained using MUCI, CA125, or Maspin as antigens, is carried out by
   (a) providing the antibody recognizing and binding to the lectin WFA-binding glycoprotein immobilized on a solid support;
   (b) contacting a sample containing the WFA-binding glycoprotein with the solid support comprising the immobilized antibody recognizing and binding to the lectin WFA-binding glycoprotein;
   (c) binding the antibody on the solid support with the lectin WFA-binding glycoprotein in the sample;
   (d) overlaying the antibody bound to the lectin WFA-binding glycoprotein with the labeled lectin WFA; and
   (e) detecting the presence of the lectin WFA-binding glycoprotein cancer marker by detecting binding of the antibody recognizing and binding to the lectin WFA binding glycoprotein and the lectin WFA-binding glycoprotein and the labeled lectin WFA; or by
   (a') providing the lectin WFA immobilized on a solid support;
   (b') contacting a sample containing the WFA-binding glycoprotein with the lectin WFA immobilized on the solid support;
   (c') binding the lectin WFA immobilized on the solid support with the lectin WFA-binding glycoprotein in the sample;
   (d') overlaying the lectin WFA bound to the lectin WFA-binding glycoprotein with a labeled antibody recognizing and binding to the lectin WFA-binding glycoprotein; and
   (e') detecting the presence of the lectin WFA-binding glycoprotein cancer marker by detecting the binding of the WFA lectin immobilized on the solid support and the lectin WFA-binding glycoprotein and the labeled antibody recognizing and binding to the lectin WFA-binding glycoprotein.

6. The method for detecting intrahepatic cholangiocarcinoma according to claim 5, wherein the detection of intrahepatic cholangiocarcinoma by antibody overlay or lectin WFA overlay is carried out by a lectin microarray detection means or an antibody microarray detection means using a microarray.

7. The method for detecting intrahepatic cholangiocarcinoma according to claim 1, wherein the test specimen for detecting intrahepatic cholangiocarcinoma in vitro is a clinical sample consisting of bile, or blood, or a clinical section.

* * * * *